US012213985B2

(12) United States Patent
Shah

(10) Patent No.: US 12,213,985 B2
(45) Date of Patent: Feb. 4, 2025

(54) ORAL CANNABINOID FORMULATIONS

(71) Applicant: Jazz Pharmaceuticals Research UK Limited, Sittingbourne (GB)

(72) Inventor: Harshit Shah, Cambridge (GB)

(73) Assignee: Jazz Pharmaceuticals Research UK Limited, Sittingbourne (GB)

( * ) Notice: Subject to any disclaimer, the term of this patent is extended or adjusted under 35 U.S.C. 154(b) by 0 days.

(21) Appl. No.: 17/689,245

(22) Filed: Mar. 8, 2022

(65) Prior Publication Data

US 2022/0362149 A1 Nov. 17, 2022

Related U.S. Application Data

(62) Division of application No. 16/314,569, filed as application No. PCT/GB2017/051914 on Jun. 29, 2017, now Pat. No. 11,291,631.

(30) Foreign Application Priority Data

Jul. 1, 2016 (EP) ...................................... 1611547

(51) Int. Cl.
| | | |
|---|---|---|
| *A61K 31/00* | (2006.01) | |
| *A61K 9/00* | (2006.01) | |
| *A61K 9/08* | (2006.01) | |
| *A61K 31/05* | (2006.01) | |
| *A61K 47/10* | (2017.01) | |
| *A61K 47/14* | (2017.01) | |
| *A61K 47/44* | (2017.01) | |
| *A61P 25/08* | (2006.01) | |

(52) U.S. Cl.
CPC .......... *A61K 31/658* (2023.05); *A61K 9/0095* (2013.01); *A61K 9/08* (2013.01); *A61K 31/05* (2013.01); *A61K 47/10* (2013.01); *A61K 47/14* (2013.01); *A61K 47/44* (2013.01); *A61P 25/08* (2018.01)

(58) Field of Classification Search
CPC .... A61K 31/658; A61K 47/10; A61K 9/0095; A61K 9/08
See application file for complete search history.

(56) References Cited

U.S. PATENT DOCUMENTS

| | | |
|---|---|---|
| 6,294,192 B1 | 9/2001 | Patel et al. |
| 6,403,126 B1 | 6/2002 | Webster |
| 6,949,582 B1 | 9/2005 | Wallace |
| 8,293,786 B2 | 10/2012 | Stinchcomb |
| 8,632,825 B2 | 1/2014 | Velasco Diez et al. |
| 8,673,368 B2 | 3/2014 | Guy et al. |
| 8,790,719 B2 | 7/2014 | Parolaro et al. |
| 8,808,734 B2 | 8/2014 | Winnicki |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,125,859 B2 | 9/2015 | Whalley et al. |
| 9,168,278 B2 | 10/2015 | Guy et al. |
| 9,259,449 B2 | 2/2016 | Raderman |
| 9,345,771 B2 | 5/2016 | Goskonda et al. |
| 9,474,726 B2 | 10/2016 | Guy et al. |
| 9,522,123 B2 | 12/2016 | Whalley et al. |
| 9,675,654 B2 | 6/2017 | Parolaro et al. |
| 9,730,911 B2 | 8/2017 | Verzura et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 9,962,341 B2 | 5/2018 | Stott et al. |
| 10,039,724 B2 | 8/2018 | Stott et al. |
| 10,092,525 B2 | 10/2018 | Guy et al. |
| 10,098,867 B2 | 10/2018 | Javid et al. |
| 10,111,840 B2 | 10/2018 | Guy et al. |
| 10,137,095 B2 | 11/2018 | Guy et al. |
| 10,220,005 B2 | 3/2019 | Martinez-Orgado |
| 10,226,433 B2 | 3/2019 | DiMarzo et al. |
| 10,441,617 B2 | 10/2019 | Lewis et al. |
| 10,583,096 B2 | 3/2020 | Guy et al. |
| 10,603,288 B2 | 3/2020 | Guy et al. |
| 10,653,641 B2 | 5/2020 | Robson et al. |
| 10,709,671 B2 | 7/2020 | Guy et al. |
| 10,709,673 B2 | 7/2020 | Guy et al. |
| 10,709,674 B2 | 7/2020 | Guy et al. |
| 10,729,665 B2 | 8/2020 | Whalley et al. |
| 10,758,514 B2 | 9/2020 | Liu et al. |
| 10,765,643 B2 | 9/2020 | Guy et al. |
| 10,799,467 B2 | 10/2020 | Whalley et al. |
| 10,807,777 B2 | 10/2020 | Whittle |
| 10,849,860 B2 | 12/2020 | Guy et al. |
| 10,918,608 B2 | 2/2021 | Guy et al. |
| 10,966,939 B2 | 4/2021 | Guy et al. |
| 11,000,486 B2 | 5/2021 | Liu et al. |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |

(Continued)

FOREIGN PATENT DOCUMENTS

| | | |
|---|---|---|
| AU | 2016203127 A1 | 5/2012 |
| CA | 2 737 447 A1 | 10/2012 |

(Continued)

OTHER PUBLICATIONS

[No. Author Listed], "Cannabidiol Therapy for Aicardi Syndrome" Aug. 2014, 4 pages.

(Continued)

*Primary Examiner* — Theodore R. Howell
(74) *Attorney, Agent, or Firm* — COOLEY LLP

(57) ABSTRACT

The present invention relates to a cannabinoid containing oral solution. Preferably the oral solution comprises a cannabinoid, a lipid solvent, a sweetener and ethanol, characterised in that the sweetener is an ultrahigh potency sweetener.

27 Claims, No Drawings

(56) References Cited

U.S. PATENT DOCUMENTS

| | | | |
|---|---|---|---|
| 11,147,783 B2 | 10/2021 | Stott et al. | |
| 11,154,516 B2 | 10/2021 | Guy et al. | |
| 11,154,517 B2 | 10/2021 | Wright et al. | |
| 11,160,757 B1 | 11/2021 | Wilkhu et al. | |
| 11,160,795 B2 | 11/2021 | Guy et al. | |
| 11,207,292 B2 | 12/2021 | Guy et al. | |
| 11,229,612 B2 | 1/2022 | Wright et al. | |
| 11,291,631 B2 | 4/2022 | Shah | |
| 11,311,498 B2 | 4/2022 | Guy et al. | |
| 11,318,109 B2 | 5/2022 | Whalley et al. | |
| 11,357,741 B2 | 6/2022 | Guy et al. | |
| 11,400,055 B2 | 8/2022 | Guy et al. | |
| 11,406,623 B2 | 8/2022 | Guy et al. | |
| 11,413,266 B2 | 8/2022 | Biro et al. | |
| 11,419,829 B2 | 8/2022 | Whalley et al. | |
| 11,426,362 B2 | 8/2022 | Wright et al. | |
| 11,446,258 B2 | 9/2022 | Guy et al. | |
| 11,590,087 B2 | 2/2023 | Guy et al. | |
| 11,622,957 B2 * | 4/2023 | Odumosu | A61K 31/015 514/454 |
| 11,633,369 B2 | 4/2023 | Guy et al. | |
| 11,679,087 B2 | 6/2023 | Guy et al. | |
| 11,684,598 B2 | 6/2023 | Stott et al. | |
| 11,701,330 B2 | 7/2023 | Guy et al. | |
| 11,723,892 B2 * | 8/2023 | Karolchyk | A61K 47/24 514/454 |
| 11,766,411 B2 | 9/2023 | Guy et al. | |
| 11,793,770 B2 | 10/2023 | Stott et al. | |
| 11,806,319 B2 | 11/2023 | Wilkhu et al. | |
| 11,865,102 B2 | 1/2024 | Guy et al. | |
| 11,963,937 B2 * | 4/2024 | Guy | A61K 31/53 |
| 12,064,398 B2 | 8/2024 | Wright et al. | |
| 12,064,399 B2 | 8/2024 | Guy et al. | |
| 2004/0049059 A1 | 3/2004 | Muller | |
| 2004/0110828 A1 | 6/2004 | Chowdhury et al. | |
| 2004/0228921 A1 | 11/2004 | Chowdhury et al. | |
| 2005/0042172 A1 | 2/2005 | Whittle | |
| 2005/0266108 A1 | 12/2005 | Flockhart et al. | |
| 2006/0039959 A1 | 2/2006 | Wessling | |
| 2006/0257463 A1 | 11/2006 | Elsohly et al. | |
| 2007/0060638 A1 | 3/2007 | Olmstead | |
| 2007/0060639 A1 | 3/2007 | Wermeling | |
| 2008/0119544 A1 | 5/2008 | Guy et al. | |
| 2008/0188461 A1 | 8/2008 | Guan | |
| 2008/0279940 A1 | 11/2008 | Rigassi et al. | |
| 2009/0035368 A1 | 2/2009 | Moschwitzer | |
| 2009/0264063 A1 | 10/2009 | Tinsley et al. | |
| 2009/0306221 A1 | 12/2009 | Guy et al. | |
| 2010/0239693 A1 | 9/2010 | Guy et al. | |
| 2010/0317729 A1 | 12/2010 | Guy et al. | |
| 2011/0028431 A1 | 2/2011 | Zerbe et al. | |
| 2011/0038958 A1 | 2/2011 | Kikuchi et al. | |
| 2011/0082195 A1 | 4/2011 | Guy et al. | |
| 2012/0004251 A1 | 1/2012 | Whalley et al. | |
| 2012/0165402 A1 | 6/2012 | Whalley et al. | |
| 2012/0183606 A1 | 7/2012 | Bender et al. | |
| 2012/0202891 A1 | 8/2012 | Stinchcomb et al. | |
| 2012/0231083 A1 | 9/2012 | Carley et al. | |
| 2012/0270845 A1 | 10/2012 | Bannister | |
| 2013/0089600 A1 | 4/2013 | Winnicki | |
| 2013/0209483 A1 | 8/2013 | McAllister | |
| 2013/0245110 A1 | 9/2013 | Guy et al. | |
| 2013/0296398 A1 | 11/2013 | Whalley et al. | |
| 2014/0100269 A1 | 4/2014 | Goskonda et al. | |
| 2014/0110828 A1 | 4/2014 | Otremba et al. | |
| 2014/0155456 A9 | 6/2014 | Whalley et al. | |
| 2014/0243405 A1 | 8/2014 | Whalley et al. | |
| 2014/0335208 A1 | 11/2014 | Cawthorne et al. | |
| 2014/0343044 A1 | 11/2014 | Ceulemens | |
| 2015/0080443 A1 | 3/2015 | Bergeron et al. | |
| 2015/0111939 A1 | 4/2015 | Gruening et al. | |
| 2015/0181924 A1 | 7/2015 | Llamas | |
| 2015/0250733 A1 | 9/2015 | Odidi | |
| 2015/0320698 A1 | 11/2015 | Whalley et al. | |
| 2015/0335590 A1 | 11/2015 | Whalley et al. | |
| 2015/0342902 A1 | 12/2015 | Vangara et al. | |
| 2015/0343071 A1 | 12/2015 | Vangara | |
| 2015/0359755 A1 | 12/2015 | Guy et al. | |
| 2015/0359756 A1 | 12/2015 | Guy et al. | |
| 2016/0166498 A1 | 6/2016 | Anastassov | |
| 2016/0166514 A1 | 6/2016 | Guy et al. | |
| 2016/0166515 A1 | 6/2016 | Guy et al. | |
| 2016/0184258 A1 | 6/2016 | Murty et al. | |
| 2016/0213624 A1 | 7/2016 | Lindeman | |
| 2016/0220529 A1 | 8/2016 | Guy et al. | |
| 2016/0256411 A1 | 9/2016 | Aung-Din | |
| 2016/0271252 A1 | 9/2016 | Vangara et al. | |
| 2016/0346235 A1 | 12/2016 | Singh et al. | |
| 2016/0367496 A1 | 12/2016 | Vangara et al. | |
| 2017/0007551 A1 | 1/2017 | Guy et al. | |
| 2017/0119660 A1 | 5/2017 | Temtsin-Krayz et al. | |
| 2017/0172939 A1 | 6/2017 | Guy et al. | |
| 2017/0172940 A1 | 6/2017 | Guy et al. | |
| 2017/0172941 A1 | 6/2017 | Guy et al. | |
| 2017/0173043 A1 | 6/2017 | Guy et al. | |
| 2017/0173044 A1 | 6/2017 | Guy et al. | |
| 2017/0181982 A1 | 6/2017 | Guy et al. | |
| 2017/0224634 A1 | 8/2017 | Vangara et al. | |
| 2017/0231923 A1 | 8/2017 | Guy et al. | |
| 2017/0239193 A1 | 8/2017 | Guy et al. | |
| 2017/0246121 A1 | 8/2017 | Guy et al. | |
| 2017/0246622 A1 | 8/2017 | Nobiki | |
| 2017/0266126 A1 | 9/2017 | Guy et al. | |
| 2017/0273913 A1 | 9/2017 | Guy et al. | |
| 2018/0028489 A1 | 2/2018 | Vangara et al. | |
| 2018/0071210 A1 | 3/2018 | Wilkhu et al. | |
| 2018/0214412 A1 | 8/2018 | Renwick | |
| 2018/0228751 A1 | 8/2018 | Stott et al. | |
| 2018/0289665 A1 | 10/2018 | Turner et al. | |
| 2018/0338931 A1 | 11/2018 | Guy et al. | |
| 2019/0083418 A1 | 3/2019 | Guy et al. | |
| 2019/0167583 A1 | 6/2019 | Shah et al. | |
| 2019/0175547 A1 | 6/2019 | Stott et al. | |
| 2019/0240160 A1 | 8/2019 | He et al. | |
| 2019/0314296 A1 | 10/2019 | Wright et al. | |
| 2019/0321307 A1 | 10/2019 | Guy et al. | |
| 2019/0365667 A1 | 12/2019 | Wright et al. | |
| 2020/0138738 A1 | 5/2020 | Guy et al. | |
| 2020/0179303 A1 | 6/2020 | Guy et al. | |
| 2020/0206153 A1 | 7/2020 | Whalley et al. | |
| 2020/0237683 A1 | 7/2020 | Whalley et al. | |
| 2020/0297656 A1 | 9/2020 | Guy et al. | |
| 2020/0352878 A1 | 11/2020 | Guy et al. | |
| 2021/0015789 A1 | 1/2021 | Guy et al. | |
| 2021/0052512 A1 | 2/2021 | Guy et al. | |
| 2021/0059949 A1 | 3/2021 | Wilkhu et al. | |
| 2021/0059960 A1 | 3/2021 | Wilkhu et al. | |
| 2021/0059976 A1 | 3/2021 | Wilkhu et al. | |
| 2021/0069333 A1 | 3/2021 | Velasco Diez et al. | |
| 2021/0100755 A1 | 4/2021 | Whalley et al. | |
| 2021/0169824 A1 | 6/2021 | Guy et al. | |
| 2021/0177773 A1 | 6/2021 | Guy et al. | |
| 2021/0290565 A1 | 9/2021 | Guy et al. | |
| 2021/0308072 A1 | 10/2021 | Wright et al. | |
| 2021/0330636 A1 | 10/2021 | Guy et al. | |
| 2021/0330797 A1 | 10/2021 | Vangara et al. | |
| 2021/0401771 A1 | 12/2021 | Guy et al. | |
| 2022/0000800 A1 | 1/2022 | Guy et al. | |
| 2022/0008355 A1 | 1/2022 | Guy et al. | |
| 2022/0016048 A1 | 1/2022 | Guy et al. | |
| 2022/0023232 A1 | 1/2022 | Guy et al. | |
| 2022/0040155 A1 | 2/2022 | Guy et al. | |
| 2022/0062197 A1 | 3/2022 | Stott et al. | |
| 2022/0062211 A1 | 3/2022 | Stott et al. | |
| 2022/0087951 A1 | 3/2022 | Guy et al. | |
| 2022/0096397 A1 | 3/2022 | Wright et al. | |
| 2022/0168266 A1 | 6/2022 | Guy et al. | |
| 2022/0183997 A1 | 6/2022 | Guy et al. | |
| 2022/0184000 A1 | 6/2022 | Guy et al. | |
| 2022/0202738 A1 | 6/2022 | Guy et al. | |
| 2022/0211629 A1 | 7/2022 | Wilkhu et al. | |
| 2022/0226257 A1 | 7/2022 | Guy et al. | |
| 2022/0233495 A1 | 7/2022 | Silcock et al. | |
| 2022/0249396 A1 | 8/2022 | Guy et al. | |

(56) References Cited

U.S. PATENT DOCUMENTS

| | | |
|---|---|---|
| 2022/0257529 A1 | 8/2022 | Guy et al. |
| 2022/0265573 A1 | 8/2022 | Guy et al. |
| 2022/0288055 A1 | 9/2022 | Silcock et al. |
| 2022/0378715 A1 | 12/2022 | Guy et al. |
| 2022/0378738 A1 | 12/2022 | Guy et al. |
| 2022/0387347 A1 | 12/2022 | Whalley et al. |
| 2022/0395470 A1 | 12/2022 | Whalley et al. |
| 2022/0395471 A1 | 12/2022 | Guy et al. |
| 2023/0000789 A1 | 1/2023 | Guy et al. |
| 2023/0022487 A1 | 1/2023 | Guy et al. |
| 2023/0024312 A1 | 1/2023 | Whalley et al. |
| 2023/0026079 A1 | 1/2023 | Guy et al. |
| 2023/0032502 A1 | 2/2023 | Guy et al. |
| 2023/0038423 A1 | 2/2023 | Silcock et al. |
| 2023/0068885 A1 | 3/2023 | Guy et al. |
| 2023/0143812 A1 | 5/2023 | Knappertz et al. |
| 2023/0235825 A1 | 7/2023 | Thompson et al. |
| 2023/0248664 A9 | 8/2023 | Guy et al. |
| 2023/0263744 A1 | 8/2023 | Guy et al. |
| 2023/0277560 A1 | 9/2023 | Checketts et al. |
| 2023/0277561 A1 | 9/2023 | Checketts et al. |
| 2023/0277562 A1 | 9/2023 | Checketts et al. |
| 2023/0277563 A1 | 9/2023 | Checketts et al. |
| 2023/0285419 A1 | 9/2023 | Checketts et al. |
| 2023/0285420 A1 | 9/2023 | Checketts et al. |
| 2023/0285421 A1 | 9/2023 | Checketts et al. |
| 2023/0285422 A1 | 9/2023 | Checketts et al. |
| 2023/0285423 A1 | 9/2023 | Checketts et al. |
| 2023/0285424 A1 | 9/2023 | Checketts et al. |
| 2023/0285425 A1 | 9/2023 | Checketts et al. |
| 2023/0285426 A1 | 9/2023 | Checketts et al. |
| 2023/0285427 A1 | 9/2023 | Checketts et al. |
| 2023/0285428 A1 | 9/2023 | Checketts et al. |
| 2023/0301934 A1 | 9/2023 | Whalley et al. |
| 2023/0301936 A1 | 9/2023 | Guy et al. |
| 2023/0310464 A1 | 10/2023 | Checketts et al. |
| 2023/0346809 A1 | 11/2023 | Craig et al. |
| 2023/0372367 A1 | 11/2023 | Checketts et al. |
| 2023/0372368 A1 | 11/2023 | Checketts et al. |
| 2024/0016819 A1 | 1/2024 | Craig et al. |
| 2024/0025858 A1 | 1/2024 | Silcock et al. |
| 2024/0033229 A1 | 2/2024 | Guy et al. |
| 2024/0033272 A1 | 2/2024 | Checketts et al. |
| 2024/0043388 A1 | 2/2024 | Silcock et al. |
| 2024/0050452 A1 | 2/2024 | Craig et al. |
| 2024/0091241 A1 | 4/2024 | Guy et al. |
| 2024/0130981 A1 | 4/2024 | Wilkhu et al. |
| 2024/0131041 A1 | 4/2024 | Tse et al. |
| 2024/0165048 A1 | 5/2024 | Guy et al. |
| 2024/0226032 A9 | 7/2024 | Wilkhu et al. |
| 2024/0238218 A1 | 7/2024 | Silcock et al. |
| 2024/0254066 A1 | 8/2024 | Silcock et al. |
| 2024/0254072 A1 | 8/2024 | Silcock et al. |

FOREIGN PATENT DOCUMENTS

| | | |
|---|---|---|
| CA | 2 859 934 A1 | 3/2016 |
| CN | 101040855 A | 9/2007 |
| CN | 103110582 A | 5/2013 |
| CN | 104840967 A | 8/2015 |
| DE | 10 2012 105 063 A1 | 12/2013 |
| EP | 1071417 B1 | 1/2004 |
| EP | 2 448 637 B1 | 5/2012 |
| EP | 2 741 750 A1 | 6/2014 |
| GB | 2384707 A | 8/2003 |
| GB | 2434097 A | 7/2007 |
| GB | 2434312 A | 7/2007 |
| GB | 2438682 A | 12/2007 |
| GB | 2450753 A | 1/2009 |
| GB | 2456183 A | 7/2009 |
| GB | 2471523 A | 1/2011 |
| GB | 2478595 A | 9/2011 |
| GB | 2479153 A | 10/2011 |
| GB | 2448637 A | 5/2012 |
| GB | 2471565 A | 7/2012 |
| GB | 2487712 A | 8/2012 |
| GB | 2478072 B | 12/2012 |
| GB | 2478074 B | 12/2012 |
| GB | 2492487 A | 1/2013 |
| GB | 2531282 A | 4/2016 |
| GB | 2539472 A | 12/2016 |
| GB | 2551987 A | 1/2018 |
| GB | 2556960 A | 6/2018 |
| JP | 2010-270110 A | 12/2010 |
| WO | WO 99/52524 A1 | 10/1999 |
| WO | WO 01/28590 A2 | 4/2001 |
| WO | WO 2002/064109 A2 | 8/2002 |
| WO | WO 2003/099302 A1 | 12/2003 |
| WO | WO 2004/016246 A1 | 2/2004 |
| WO | WO 2004/016277 A2 | 2/2004 |
| WO | WO 2006/054057 A2 | 5/2006 |
| WO | WO 2006/133941 A2 | 12/2006 |
| WO | WO 2007/032962 A2 | 3/2007 |
| WO | WO 2007/083098 A1 | 7/2007 |
| WO | WO 2007/138322 A1 | 12/2007 |
| WO | WO 2008/019146 A2 | 2/2008 |
| WO | WO 2008/021394 A2 | 2/2008 |
| WO | WO 2008/024490 A2 | 2/2008 |
| WO | WO 2008/046905 A1 | 4/2008 |
| WO | WO 2008/094181 A3 | 8/2008 |
| WO | WO 2008/129258 A1 | 10/2008 |
| WO | WO 2008/144475 A1 | 11/2008 |
| WO | WO 2008/146006 A1 | 12/2008 |
| WO | WO 2009/007697 A1 | 1/2009 |
| WO | WO 2009/007698 A1 | 1/2009 |
| WO | WO 2009/020666 A1 | 2/2009 |
| WO | WO 2010/012506 A1 | 2/2010 |
| WO | WO 2011/001169 A1 | 1/2011 |
| WO | WO 2011/002285 A1 | 1/2011 |
| WO | WO 2011/121351 A1 | 10/2011 |
| WO | WO 2012/033478 A1 | 3/2012 |
| WO | WO 2012/093255 A1 | 7/2012 |
| WO | WO 2013/024373 A1 | 2/2013 |
| WO | WO 2013/032351 A1 | 3/2013 |
| WO | WO 2014/146699 A1 | 9/2014 |
| WO | WO 2015/142501 A1 | 9/2015 |
| WO | WO 2015/184127 A2 | 12/2015 |
| WO | WO 2015/193667 A1 | 12/2015 |
| WO | WO 2015/193668 A1 | 12/2015 |
| WO | WO 2016/059405 A1 | 4/2016 |
| WO | WO 2016/084075 A1 | 6/2016 |
| WO | WO 2016/118391 A1 | 7/2016 |
| WO | WO 2016/141056 A1 | 9/2016 |
| WO | WO 2016/147186 A1 | 9/2016 |
| WO | WO 2016/022936 A1 | 11/2016 |
| WO | WO 2016/199148 A1 | 12/2016 |
| WO | WO 2017/059859 A1 | 4/2017 |
| WO | WO 2017/072762 A1 | 5/2017 |
| WO | WO 2017/072774 A1 | 5/2017 |
| WO | WO 2017/168138 A1 | 10/2017 |
| WO | WO 2018/002636 A1 | 1/2018 |
| WO | WO 2018/002637 A1 | 1/2018 |
| WO | WO 2018/002665 A1 | 1/2018 |
| WO | WO 2018/035030 A1 | 2/2018 |
| WO | WO 2018/037203 A1 | 3/2018 |
| WO | WO 2019/082171 A1 | 5/2019 |
| WO | WO 2019/135075 A1 | 7/2019 |
| WO | WO 2019/135076 A1 | 7/2019 |
| WO | WO 2019/135077 A1 | 7/2019 |
| WO | WO 2019/159174 A1 | 8/2019 |
| WO | WO 2020/016653 A1 | 1/2020 |
| WO | WO 2020/240184 A1 | 12/2020 |

OTHER PUBLICATIONS

[No. Author Listed], Cover and Table of Contents, J Pharmacology and Exp Therapeutics, Feb. 2010, 332(2), 4 pages.

[No. Author Listed], "Missouri House passes cannabis extract legislation," Kansas City Star, 2014, https://kansascity.com/news/politics-government/article346747.html, 2 pages.

[Author Unknown], Cannabinoid. Wikipedia. Retrieved on Jul. 9, 2015, from https://en.wikipedia.org/wiki/Cannabinoid, 15 pages.

(56) References Cited

OTHER PUBLICATIONS

[Author Unknown]], High Times [online]; 2017, downloaded from: https://hightimes.com/edibles/2017-socal-canabis-cup-top-10-edibles/ on Dec. 15, 2022, 3 pages.
[ANONYMOUS], Potvalet [online]; 2017; downloaded from https://www.pitvalet.com/products/cbd-thc-gel-caps-1-1/ on Dec. 15, 2022, 2 pages.
Alger, "Not too excited? Thank your endocannabinoids," Neuron, 51(4):393-595 (2006).
American Epilepsy Society, "Three Studies Shed New Light on the Effectiveness of Cannabis in Epilepsy," Oct. 14, 2014, 2 pages.
Ames et al., "Anticonvulsant effect of cannabidiol," S Afr Med J. Jan. 4, 1986; 69(1): 14, 1 page.
Appendino, J. P. et al., "Position Statement on the Use of Medical Cannabis for the Treatment of Epilepsy in Canada," Can J. Neurol. Sci., 33:783-786 (2006).
AU Re-examination report - standard patent for Australian Patent No. 2012204800, dated May 3, 2019, 7 pages.
AU Third Party Observations for Application No. AU20 l 2314128, mailed Mar. 19, 2015, 51 pages.
Astruc-Diaz, F., "Cannabinoids delivery systems based on supramolecular inclusion complexes and polymeric nanocapsules for treatment of neuropathic pain," Université Claude Bernard—Lyon I, 2012, submitted on Jan. 23, 2014; https://tel.archives-ouvertes.fr/tel-00935588 [accessed Nov. 1, 2019], 278 pages.
Arain, "Pregabalin in the management of partial epilepsy," Neuropsychiatr Dis Treat., 407-13 (2009); Epub Aug. 2, 20090.
Arimanoglou et al., "All children who experience epileptic falls do not necessarily have Lennox-Gastaut syndrome . . . but many do," Epileptic Discord, 13: S3-S13 (2011).
Arslan, A. & Tirnaksiz, F., "Self-emulsifying Drug Delivery Systems," F Abad J Pharm Sci, 38(1):55-64 (2013).
Avoli et al. "Cellular and molecular mechanisms of epilepsy in the human brain," Prog Neurobiol., 77(3):166-200 (2005).
Bakhsh, "Pregabalin in the management of partial epilepsy," Miftaah-al-Khazaain, 1930:607-608, with English translation, 4 pages.
Bancaud, "Proposal for Revised Clinical and Electroencephalographic Classification of Epileptic Seizures," Epilepsia, 22(4):489-501 (1981).
Banerjee et al., "Case Report: Aicardi syndrome: A report of five Indian cases," Neurology India, 54(1):91-93 (2006).
Barker-Haliski et al. "How Clinical Development Can, and Should Inform Translational Science," Neuron, 84:582-593 (2014).
BASF Pharma Ingredients Lutrol® F68 NF [online]. Retrieved on Feb. 22, 2022 from: http://www2.basf.US/Pharma/pdf/Lutrol_F_68.pdf, 2001, 1 page.
Benowitz et al. "Metabolic and Psychophysiologic studies of cannabidiol hexobarbital interaction," Clin Pharmacol Ther., 28(1):115-120 (1980).
Benowitz & Jones, "Cardiovascular and metabolic considerations in prolonged cannabinoid administration in man," J Clin Pharm, 21:214S-223S (1981).
Bertram, "The Relevance of Kindling for Human Epilepsy," Epilepsia, 48(Suppl. 2):65-74 (2007).
Bhatt, V. P. & Vashishtha, D. P., "Indigenous plants in traditional healthcare system in Kedarnath valley of western Himalaya," Indian J Tradit Knowl., 7(2):300-310 (2000).
Bhattacharyya, et al. "Modulation of mediotemporal and ventrostriatal function in humans by Delta9-tetrahydrocannabinol: a neural basis for the effects of Cannabis sativa on learning and psychosis," Arch Gen Psychiatry, 66(4): 442-451 (2009); doi: 10.1001/archgenpsychiatry.2009 .17.
Bipolar Health Group (Charlotte's Web Hemp Remedy, available online at http:/bipolarhealthgroup.org/index.php/charlottes-web-hemp-remedy/, accessed Sep. 6, 2017, 6 pages.
cdc.gov [online], "2 to 20 years: girls Stature-for-age and Weigh-for-age percentiles," National Center for Health Statistics and National Center for Chronic Disease Prevention and Health Promotion, last modified Nov. 2000, <https://www.cdc.gov/growthcharts/data/set1clinical/cj4aa022.pdf>, 1 page.
Booth, "Legalization's opening of medical pot research is dream and nightmare," Denver Post, Dec. 14, 2013, 6 pages.
Bostanci, M. O. & Bagirici, F., "The effects of octanol on penicillin induced epileptiform activity in rats: an in vivo study," Epilepsy Research, 71:188-194 (2006).
Braida, et al., "Post-ischemic treatment with cannabidiol prevents electroencephalographic flattening, hyperlocomotion and neuronal injury in gerbils," Neuroscience Letters., 346:61-64 (2003).
Brust, J. C. M. et al., "Marijuana use and the risk of new onset seizures," Trans Am Clin Climatol Assoc., 103:176-181 (1992).
Carlini et al., "Hypnotic and antiepileptic effects of cannabidiol," J Clin Pharmacol., 21:417S-427S (1981).
Castel-Branco et al. "The Maximal Electroshock Seizure (MES) Model in the Preclinical 98. Assessment of Potential New Anti epileptic Drugs," Methods Find Exp Clin Pharmacol., 31 (2); 101-106, 2009.
Charlotte's Web [online], "When to expect Results from CW Hemp Oil," Mar. 13, 2017, retrieved on May 21, 2018, URL https://www.cwhemp.com/blog/expecting-results-from-hemp, 6 pages.
Charlotte's Web [online], "Whole-Plant Cannabinoids Outperform Single Molecule Compounds," CWHemp.com, Jan. 11, 2017, retrieved on Jun. 16, 2017, URL https://www.cwhemp.com/blog/whole-plant-cw-hemp-cannabinoids, 6 pages.
ChildNeurologyFoundation.org [online], "Disorder Directory: Learn from the Experts—LGS (Lennon-Gastaut Syndrome)," Child Neurology Foundation, available on or before Sep. 6, 2015, retrieved on May 21, 2018; URL http://www.childneurologyfoundation.org/disorders/ lgs-Lennox-gastaut-syndrome, 10 pages.
Chiron, C. & Dulac, O., "The Pharmacologic Treatment of Dravet Syndrome," Epilepsia, 52 (Suppl. 2):72- 75 (2011).
Chiu, P. et al., "The Influence of Cannabidiol and A-Tetrahydro-cannabinol on Cobalt Epilepsy in Rats," Epilepsia, 20:365-375 (1979).
Chiu, P. et al., "The influence of delta9-tetrahydrocannabinol, cannabinol and cannabidiol on tissue oxygen consumption," Res Commun 12, No. 2, pp. 267-286, 1977.
Chou, "Theoretical basis, experimental design, and computerized simulation of synergism and antagonism in drug combination studies," Pharmacol Rev., 58(3):621-681 (2006).
Combined Search and Examination Report mailed Jan. 4, 2012, for Application No. GB 1116789.7, 8 pages.
Combined Search and Examination Report mailed Mar. 25, 2011, for Application No. GB 1100043.7, 8 pages.
Combined Search and Examination Report mailed Sep. 5, 2014 for Application No. GB 1414813.4, 8 pages.
Combined Search and Examination Report Under Sections 17 and 18 (3) for International Application No. GB1121919.3, dated Feb. 29, 2012, 8 pages.
Combined Search and Examination Report Under Sections 17 and 18 (3) for International Application No. GB 141077 1 .8, dated Feb. 27, 2018, 7 pages.
Combined Search and Examination Report Under Sections 17 and 18 (3) for International Application No. GB 1418166.3, dated Jul. 2, 2015, 8 pages.
Combined Search and Examination Report Under Sections 17 and 18 (3) for International Application No. GB 1418170.5, dated Jul. 2, 2015, 6 pages.
Combined Search and Examination Report Under Sections 17 and 18 (3) for International Application No. GB 1418171.3, dated Jun. 29, 2015, 8 pages.
Combined Search and Examination Report Under Sections 17 and 18 (3) for International Application No. GB 1506550.1, dated Feb. 5, 2016, 9 pages.
Combined Search and Examination Report for GB Application No. GB1514079.1, dated May 4, 2016, 9 pages.
Combined Search and Examination Report for GB Application No. GB160544.8, dated Jan. 12, 2017, 6 pages.
Conry et al., "Clobazam in the treatment of Lennox-Gastaut syndrome," Epilepsia, 50:1158-1166 (2009).
Consroe et al. Chapter 12, "Potential Role of Cannabinoids for Therapy of Neurological Disorders," in Marijuana Cannabinoids: Neurobiology and Neurophysiology, Ed. L. Murphy (1992), 72 pages.

(56) References Cited

OTHER PUBLICATIONS

Consroe et al. "Anticonvulsant drug antagonism of delta9tetrahydrocannabinol-induced seizures in rabbits," Res Commun Chem Pathol Pharmacol., 16(1):1-13 (1977).
Consroe et al. "Anticonvulsant interaction of cannabidiol and ethosuximide in rats," J Pharm Pharmacol., 29(8):500-501 (1977). doi:10.1111/j.2042-7158.1977.tb11378.x.
Consroe et al. "Anticonvulsant nature of marihuana smoking," JAMA, 234(3):306-307 (1975).
Consroe, P. & Wolkin, A., "Cannabidiol—antiepileptic drug comparisons and interactions in experimentally induced seizures in rats," J Pharmacol Exp Ther. Apr. 1977;201(1):26-32.
Consroe et al. "Effects of cannabidiol on behavioral seizures caused by convulsant drugs or current in mice," Eur J Pharmacol., 83(3-4):293-298 (1982).
Consroe, P. & Snider, S. R., "Chapter 2. Therapeutic Potential of Cannabinoids in Neurological disorders," Cannabinoids as Therapeutic Agents, R. Mechoulam, Ed., pp. 21-49 (1986).
Consroe et al., "Controlled clinical trial of cannabidiol in Huntington's Disease," Pharmacology Biochemistry & Behavior, 40:701-708 (1991).
EPO Annex to the Communication in Opposition for European Appln. No. 10734541.5, dated Jan. 28, 2016, 5 pages.
EPO Auxiliary Requests to the File in European Patent No. EP2448637, dated Nov. 2, 2016, 40 pages.
EPO Communication of a Notice of Opposition in European Appln. No. 10734541.5, dated Dec. 17, 2014, 1 page.
EPO Communication Pursuant to Article 94(3) EPC in European Appln. No. 10734541.5, dated Oct. 23, 2012, 3 pages.
EPO Interlocutory Decision in Opposition in European Application No. EP2448637, Dec. 15, 2016, 2 pages.
EPO Letter from Opponent Regarding Oral Proceedings in European Patent No. EP2448637, dated Oct. 20, 2016, 5 pages.
EPO Notice of Appeal in European Patent No. EP2448637, dated Feb. 14, 2017, 5 pages.
EPO Notice of Opposition to a European Patent No. EP2448637, dated Dec. 5, 2014, 20 pages.
EPO Opposition, Expert Statement of Dr. Emma Louise Cheetham in European Appln. No. EP10734541.5, dated Nov. 4, 2016, 1 page.
EPO Opposition, Expert Statement of Professor Anthony G. Marson in European Appln. No. EP10734541.5, dated Jun. 14, 2016, 9 pages.
EPO Opposition, Expert Statement of Professor Benjamin J. Whalley in European Appln. No. EP10734541.5, Sep. 9, 2016, 11 pages.
EPO Opposition, Expert Statement of Vincenzo DiMarzo in European Appln. No. EP10734541.5, Sep. 9, 2016, 10 pages.
EPO Opposition, Supplemental Expert Statement of Professor Benjamin J. Whalley, dated Nov. 4, 2016, 9 pages.
EPO Reply of the Patent Proprietor to the Notice(s) of Opposition in European Patent No. 2448637, dated May 28, 2015, 12 pages.
EPO Reply to Examination Report in European Patent Application No. 10734541.5, dated Feb. 15, 2013, 54 pages.
EPO Reply to Opponent's Written Submissions in European Patent No. EP2448637, dated Nov. 4, 2016, 13 pages.
EPO Reply to Opponent's Written Submissions in European Patent No. EP2448637, dated Oct. 18, 2016, 5 pages.
EPO Reply to Preliminary Opinion and Opponent's Observations in European Patent No. EP2448637, dated Sep. 9, 2016, 65 pages.
EPO Reply to Proprietor's Statement of Grounds of Appeal in European Patent No. EP2448637, dated Sep. 8, 2017, 5 pages.
EPO Response to the Statement of Grounds of Appeal in European Patent No. EP2448637, dated Sep. 5, 2017, 17 pages.
EPO Statement of Grounds of Appeal in European Appln. No. 10734541.5, dated Apr. 21, 2017, 14 pages.
EPO Statement of Grounds of Appeal in European Appln. No. 10734541.5, dated Apr. 12, 2017, 6 pages.
EPO Statement of Opposition in European Appln. No. 10734541.5, dated Dec. 5, 2014, 14 pages.
EPO Third Party Observations for Application No. EP10734541.5, mailed Apr. 3, 2017, 3 pages.

EPO Third Party Observations for Application No. EP11712658.1, dated Nov. 22, 2013, 14 pages.
Cortesi et al. "Potential therapeutical effects of cannabidiol in children with pharmacoresistant epilepsy," Med Hypotheses, 68(4):920-921 2007). Epub Nov. 1, 20066.
Cortez & Snead, "Chapter 10: Pharmacologic Models of Generalized Absence Seizures in Rodents," Models of Seizures and Epilepsy, 111-126 (2006).
Crespel et al., "Lennox-Gastaut Syndrome," Chapter 14, in Epileptic Syndromes in Infancy, Childhood, and Adolescence, 5th Edition, 2012, ed. M. Bureau, et al., pp. 189-216.
Crodesta F10 [online] retrieved on Feb. 4, 23 from: https://www.ulprospector.com/en/na/PersonalCare/Detail/134/30883/Crodesta-F10; 2 pages. (Year: 2023).
Cunha et al. "Chronic administration of cannabidiol to healthy volunteers and epileptic patients." Pharmacology, 21(3): 175-85 (1980).
Curia et al., "The pilocarpine model of temporal lobe epilepsy," J Neuroscience Methods, 172(2-4): 143-157 (2008).
Czapinski, et al. "Randomized 36-month comparative study of valproic acid (VPA), phenytoin (PHT), phenobarbital (PB) and carbamazepine (CBZ) efficacy in patients with newly diagnosed epilepsy with partial complex seizures." J Neurolog Sci., 150: S162 (1997), 2 pages.
Dasa et al. "Key Attributes of TKDL: Ganja," Brhat Nighantu Ratnakara (Saligramanighantubhusanam), RS/4336, vol. IV. 1997:170, with English translation, 5 pages.
Davis et al. "Antiepileptic action of marijuana-active substances," Federation Proceedings, 8:284-285 (1949).
Davis et al. "A predominant role for inhibition of the adenylate cyclase/protein kinase A pathway in ERK activation by cannabinoid receptor 1 in NIE-115 neuroblastoma cells." J Biol Chem. 278(49):48973-80 (2003). Epub Sep. 2, 20039.
De Meijer, "Chapter 5: The Chemical Phenotypes (Chemotypes) of Cannabis," Handbook of Cannabis, Ed. Roger G. Pertwee, pp. 89-110 (2014).
De Oliveira, et al. "Anticonvulsant activity of β-caryophyllene against pentylenetetrazol-induced seizures." Epilepsy Behav., 56:26-31 (2016). doi: 10.1016/j.yebeh.2015.12.040.
Deshpande, et al. "Cannabinoid CB 1 receptor antagonists cause status epilepticus-like activity in the hippocampal neuronal culture model of acquired epilepsy." Neurosci Lett., 41 |(I): 1-6 (2007). Epub Nov. 1, 2006.
Devinsky, Orrin, M.D. of the Department of Neurology for NYU Langone School of Medicine presents his talk on "Cannabidiols: A Brief History," at NYU School of Medicine's Cannabidiol Conference (Oct. 4, 2013). Video published online. < http://faces.med.nyu.edu/research-education/cannabidiol-conference>, 16 pages.
Devinsky, et al., "Cannabidiol: Pharmacology and potential therapeutic role in epilepsy and other neuropsychiatric disorders," Epilepsia, 55(6):791-802 (2014).
Devinsky et al., "Trial of Cannabidiol for Drug-Resistant Seizures in the Dravet Syndrome," N Engl J Med, 376(21):2011-2020 (2017).
Dravet, C., "The core Dravet syndrome phenotype," Epilepsia. 52 Suppl 2:3-9, 2011. doi: 10.1111/j.1528-1167.2011.02994. x.
Dreifus et al., "Proposal for Revised Clinical and Electroencephalographic Classification of Epileptic Seizures," Epilepsie, 22:489-501 (1981).
Dulac, "Vigabatrin in Childhood Epilepsy," J. Child Neurolog., 6(Supplement 2), S30-S37 (1991).
Dulac, "Use of Lamotrigine in Lennox-Gastaut and Related Epilepsy Syndromes," J. Child Neurolog., 12(Supplement 1), S23-S29 (1997).
Eadie, "Shortcomings in the current treatment of epilepsy," Expert Rev Neurother, 12(12): 1419-27 (2012).
Eggers, "Temporal lobe epilepsy is a disease of faulty neuronal resonators rather than oscillators, and all seizures are provoked, usually by stress," Med Hypotheses., 69(6): 1284-9 (2007).
Elsohly and Gul. "Constituents of Cannabis Sariva," Chapter 1, Handbook of Cannabis, ed. Roger G. Pertwee, pp. 3-22 (2014).
Engel. "Report of the ILAE classification core group." Epilepsia. Sep. 2006;47(9): 1558-68.

(56) References Cited

OTHER PUBLICATIONS

Engel, "Chapter 1: What Should be Modeled?" In Models Seizure Epilepsy, 2006, 14 pages.
EPIDIOLEX® (cannabidiol) oral solution, CV, Prescribing Information, 2018, 30 pages; https://www.accessdata.fda.gov/drugsatfda_docs/label/2018/210365lbl.pdf.
Fariello. "Parenteral Penicillin in Rats: An Experimental Model of Multifocal Epilepsy," Epilepsia, 17:217-222 (1976).
FDA [online]. "Warning Letters and Test Results for Cannabidiol-Related Products," 2015 Warning Letters, retrieved on Nov. 14, 2017, URL <https://www.fda.gov/newsevents/publichealthfocus/ucm484109.htm>, 4 pages.
FDA [online]. "Warning Letters and Test Results for Cannabidiol-Related Products," 2016 Warning Letters, retrieved on Nov. 14, 2017, URL <https://www.fda.gov/newsevents/publichealthfocus/ucm484109.htm>, 4 pages.
Ferdinand, et al., "Cannabis—psychosis pathway independent of other types of psychopathology," Schizophr Res., 79(2-3):289-295 (2005).
Fisher et al., "The impact of epilepsy from the patient's perspective I. Descriptions and subjective perceptions," Epilepsy Res. Aug. 2000;41(1):39-51.
Gabor et al. "Lorazepam versus phenobarbital : Candidates for drug of choice for treatment of status epilepticus," J Epilepsy. Jan. 1990;3(1):3-6.
Gallily, et al., "Overcoming the Bell-Shaped Dose-Response of Cannabidiol by Using Cannabis Extract Enriched in Cannabidiol," Pharmacology & Pharmacy, 6:75 (Jan. 2015), 12 pages.
Gardner [online], "Comes Now Epidiolex (FDA Approves IND Studies of CBD)," BeyondTHC.com, Oct. 22, 2013, retrieved on Jan. 31, 2018, URL http://www.beyondthc.com/comes-now-epidiolex-fda-approves-ind-studies-of-cbd, 4 pages.
Gastaut, "Clinical and electroencephalographical classification of epileptic seizures" Epilepsia, Mar. 1970;Il(I): 102-13.
Gedde [online], "Clinical Experience with Cannabis in Treatment-Resistant Pediatric Epilepsy," Marijuana for Medical Professionals Conference, Sep. 9-11, 2014, URL <http://www.theroc.US/images/gedde_presentation.pdf, Sep. 9-11, 2014>, 45 pages.
Gedde et al., "3.330: Whole Cannabis Extract of High Concentration Cannabidiol May Calm Seizures in Highly Refractory Pediatric Epilepsies," American Epilepsy Society, Dec. 2013, 449-450.
Geffrey et al. "Cannabidiol (CBD) Treatment for Refractory Epilepsy," American Epilepsy Society, Annual Meeting Abstract 2.427, 2014, retrieved on Feb. 10, 2017, URL <https://www.aesnet.org/meetings_events/annual_meeting_abstracts/view/1868979>, 2 pages.
Green, "CBD: An Unconventional Therapy," available online at http://nugs.com/article/cbd-an unconventional-therapy.html, published Mar. 24, 2014, 5 pages.
Gresham et al."Treating Lennox-Gastaut syndrome in epileptic pediatric patients with third generation rufinamide," Neuropsychiatr Dis Treat., 6:639-645, Oct. 5, 2010.
Gross et al. "Marijuana use and epilepsy: prevalence in patients of a tertiary care epilepsy center," Neurology, Jun. 8, 2004; 62(11 ):2095-7.
Grotenhermen, "Epilepsiebehandlung des Angelman-Syndromes mit CBD (Cannabidiol) (Epilepsy treatment of Angelman syndrome with CBD (cannabidiol)," Angelman e. V., Jan. 2015, retrieved on Jun. 7, 2019, URL <http://s8a5e4d6fcfb04b6.jimcontent.com/download/version/ 1472724876/module/9873059694/name/Epilepsiebehandlung%20durch%20CBD.pdf> (with Machine English translation), 8 pages.
Guerrini et al., "Lamotrigine and Seizure Aggravation in Severe Myoclonic Epilepsy," Epilepsia, 39(5):508- 512 (1998).
Guidance for Industry, Botanical Drug Development, U.S. Department of Health and Human Services, Food and Drug Administration, Center for Drug Evaluation and Research (CDER) Dec. 2016, Pharmaceutical Quality/CMC, 34 pages; https://www.fda.gov/media/93113/download.
Guimaraes, et al. "Antianxiety effect of cannabidiol in the elevated plus-maze," Psychopharmacology (Berl). 1990;100(4):558-9. doi: 10.1007/BF02244012.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL https://www.gwpharm.com/about-US/news/gw-pharmaceuticals-announces-epidiolex%C2%AE-receives-fast-track-designation-fda-treatment, 2 pages.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-US/news/gw-pharmaceuticals-announces-physician-reports- epidiolex%C2%AE-treatment-effect-children>, 8 pages.
GWPharm [online], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-US/news/gw-pharmaceuticals-provides-update-orphan-program-childhood-epilepsy-epidiolex%C2%AE>, 5 pages.
GWPharm [online], "GW Pharmaceuticals Receives Orphan Drug Designation by FDA for Epidiolex® in the treatment of Lennox-Gastaut Syndrome," GW Pharmaceuticals Press Release, Feb. 28, 2014, retrieved on Feb. 10, 2017, URL <https://www.gwpharm.com/about-US/news/gw-pharmaceuticals-receives- orphan-drug-designation-fda-epidiolex%C2%AE-treatment-lennox>, 4 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwpharm.com/about-US/news/gw-pharmaceuticals-provides-update- orphan-program-childhood-epilepsy-epidiolex%C2%AE>, 5 pages.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-US/news/gw-pharmaceuticals-announces-preliminary-results-phase-2a-study-its-pipeline-compound>, 5 pages.
Heinemann et al., "An Overview of in Vitro Seizure Models in Acute and Organotypic Slices," Chapter 4, 35-44 (2006).
Hempel, B. J. et al., "An assessment of sex differences in A9-tetrahydrocannabinol (THC) taste and place conditioning," Pharmacology, Biochemistry and Behavior, 153:69-75 (2017).
Hill et al. "A9-Tetrahydrocannabivarin suppresses in vitro epileptiform and in vivo seizure activity in adult rats." Epilepsia. Aug. 2010;51(8): 1522-32. doi: 10.1111/j.1528-1167.2010.02523.x. Epub Feb. 2, 20106.
Hill, "Cannabidivarin-rich cannabis extracts are anticonvulsant in mouse and rat via a CB 1 receptor-independent mechanism," British Journal of Pharmacology, Oct. 2013, 170(3): 679-692.
Hill et al., "Cannabidivarin is anticonvulsant in mouse and rat," Br J Pharmacol, 167(8): 1629-1642 (2012).
Holmes et al., "Choosing the correct AED: From Animal Studies to the Clinic," Pediatr Neurol. Mar. 2008; 38(3): 151-162.
Iannotti et al. "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability."ACS Chem Neurosci. Nov. 1, 20149;5(11): 1131-41. doi: 10.1021/cn5000524.
ICE Epilepsy Alliance, the Dravet Syndrome Spectrum, Nov. 2, 2008, 10 pages.
*Insys Development Company, Inc. v. GW Pharma Limited and Otsuka Pharmaceutical Co., Ltd.,* Decision in IPR2017-00503, U.S. Pat. No. 9,066,920, dated Jul. 7, 2017, 26 pages.
*Insys Development Company, Inc. v. GW Pharma Limited and Otsuka Pharmaceutical Co., Ltd.,* Declaration by Mark Polyakov, IPR2017-00503, U.S. Pat. No. 9,066,920, dated May 29, 2018, 1 page.

(56) References Cited

OTHER PUBLICATIONS

*Insys Development Company, Inc. v. GW Pharma Limited and Otsuka Pharmaceutical Co., Ltd.,* Declaration of Professor Anthony G. Marson in IPR2017-00503, U.S. Pat. No. 9,066,920, dated Dec. 13, 2016, 28 pages.
*Insys Development Company, Inc. v. GW Pharma Limited and Otsuka Pharmaceutical Co., Ltd.,* Declaration of Professor H. Steve White in IPR2017-00503, U.S. Pat. No. 9,066,920, dated Oct. 24, 2017, 69 pages.
*Insys Development Company, Inc. v. GW Pharma Limited and Otsuka Pharmaceutical Co., Ltd.,* Declaration of Professor Leslie Benet in IPR2017-00503, U.S. Pat. No. 9,066,920, dated Nov. 22, 2016, 18 pages.
*Insys Development Company, Inc. v. GW Pharma Limited and Otsuka Pharmaceutical Co., Ltd.,* Deposition of H. Steve White, dated Dec. 13, 2016, 50 pages.
*Insys Development Company, Inc. v. GW Pharma Limited and Otsuka Pharmaceutical Co., Ltd.,* Final Written Decision in IPR2017-00503, U.S. Pat. No. 9,066,920, dated Jan. 3, 2019, 40 pages.
*Insys Development Company, Inc. v. GW Pharma Limited and Otsuka Pharmaceutical Co., Ltd.,* Petitioner's Brief Regarding Ground III of the IPR, IPR2017-00503, U.S. Pat. No. 9,066,920, dated May 29, 2018, 45 pages.
*Insys Development Company, Inc. v. GW Pharma Limited and Otsuka Pharmaceutical Co., Ltd.,* Petition for Inter Partes Review, IPR2017-00503, U.S. Pat. No. 9,066,920, dated Dec. 16, 2016, 78 pages.
*Insys Development Company, Inc. v. GW Pharma Limited and Otsuka Pharmaceutical Co., Ltd.,* Petitioner's Reply to Patent Owner's Response, IPR2017-00503, U.S. Pat. No. 9,066,920, dated Jun. 19, 2018, 6 pages.
*Insys Development Company, Inc. v. GW Pharma Limited and Otsuka Pharmaceutical Co., Ltd.,* Petitioner's Reply to Response in IPR2017-00503, U.S. Pat. No. 9,066,920, dated Jan. 19, 2018, 36 pages.
International Preliminary Report on Patentability for International Application No. PCT/GB2017/052229, dated Feb. 26, 2019, 7 pages.
International Search Report and Written Opinion for International Application No. PCT/GB2017/052229, dated Oct. 6, 2017, 10 pages.
International Preliminary Report on Patentability for International Application No. PCT/GB2010/051066, dated Jun. 9, 2011, 6 pages.
International Preliminary Report on Patentability for International Application No. PCT/GB2012/052284, dated Dec. 12, 2013, 12 pages.
International Preliminary Report on Patentability for International Application No. PCT/GB2015/051775, dated Aug. 10, 2016, 9 pages.
International Preliminary Report on Patentability for International Application No. PCT/GB2015/053030, dated Apr. 18, 2017, 6 pages.
International Preliminary Report on Patentability for International Application No. PCT/US2017/050868, dated Oct. 11, 2018, 7 pages.
International Search Report and Written Opinion for International Application No. PCT/US2017/050868, dated Aug. 6, 2017, 14 pages.
International Search Report and Written Opinion for International Application No. PCT/US2017/051943, dated Sep. 12, 2017, 10 pages.
International Search Report and Written Opinion for International Application No. PCT/GB2017/051913, dated Sep. 15, 2017, 9 pages.
International Search Report and Written Opinion for International Application No. PCT/GB2017/051914, dated Sep. 12, 2017, 10 pages.
International Search Report and Written Opinion mailed Aug. 25, 2015 for International Application No. PCT/GB2015/051776, 11 pages.
International Search Report and Written Opinion mailed Aug. 26, 2015 for International Application No. PCT/GB2015/051775, 11 pages.
International Search Report and Written Opinion mailed Dec. 13, 2010 for International Application No. PCT/GB2010/051066, 8 pages.
International Search Report and Written Opinion mailed May 30, 2011 for International Application No. PCT/GB2011/050649, 15 pages.
International Search Report mailed Nov. 16, 2010 for International Application No. PCT/GB2010/051066, 8 pages.
International Search Report mailed Feb. 24, 2012 for International Application No. PCT/GB2012/050002, 3 pages.
International Search Report and Written Opinion mailed Oct. 25, 2016 for International Application No. PCT/GB2016/052340, 12 pages.
IUPHAR/BPS Guide to Pharmacology [online], "Entry for Δ 9-tetrahydrocannabidiol," available on or before Mar. 29, 2016, retrieved on Jun. 20, 2018, URL <http://www.guidetopharmacology.org/GRAC/LigandDisplayForward?tab=biology&ligandID=242>, 2 pages.
Iuvone et al., "Neuroprotective effect of cannabidiol, a non-psychoactive component from Cannabis sativa, on beta-amyloid-induced toxicity in PC12 cells." J Neurochem. Apr. 2004; 89(1): 134-41.
Izzo et al., "Non-psychotropic plant cannabinoids: new therapeutic opportunities from an ancient herb." Trends in Pharmacological Sciences. 30(10): 515-527 (2009).
Jablan, J. & Jug, M., "Development of Eudragit® S100 based pH-responsive microspheres of zaleplon by spray-drying: Tailoring the drug release properties," Powder Technology, 283 (2015) 334-343.
Jacobson, "Survey of Current Cannabidiol Use in Pediatric Treatment-Resistant Epilepsy," Apr. 22, 2013, 1 page.
Jeavons et al., "Sodium valproate in treatment of epilepsy." Br Med J. Jun. 1, 19745;2(5919):584-6.
Jones et al. [online], Info & Metrics / Article Information," Cannabidiol Displays Antiepileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info, 9 pages.
Jones et al., "Cannabidiol Displays Antiepileptiform and Antiseizure Properties in Vitro and in Vivo," J Pharmacol Exp Ther., 332(2):559-577 (2010).
Joy, et al. "Marijuana and Medicine. Assessing the Science Base." National Academy Press. Washington D.C. 1999, 170 pages.
Kahan, et al. "Risk of selection bias in randomized trials," Trials, 16:405 (2015), 7 pages.
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
Karler et al. "The cannabinoids as potential antiepileptics," J Clin Pharmacol, 21(8-9 Suppl): 437S-447S (1981).
Karler et al., "The anticonvulsant activity of cannabidiol and cannabinol," Life Science, 13:1527-1531 (1973).
Kelley, et al. "Doose syndrome (myoclonic-astatic epilepsy): 40 years of progress," Developmental Medicine & Child Neurology, Aug. 2010, 52: 988-993.
Khan et al., "Key Attributes of TKDL: Laooq-e-Quinnab/Barai Zeequn-Nafs," Khazaain-al-Advia, 1911 (with English translation), 2 pages.
Khan et al., Key Attributes of TKDL: Nushka-e-Qutoor, Muheet-e-Azam, 1887 (with English translation), 2 pages.
Khan et al., "Key Attributes of TKDL: Sufoof-e-Qinnab Barae Waja," Khazaain-al-Advia, 1911, (with English translation), 5 pages.
Khan et al., "Key Attributes of TKDL: Usaara-e-Qinnab Barai Qoolanj," Khazaain-al-Advia, 1911 (with English translation), 6 pages.
Khan et al., "Key Attributes of TKDL: Zimad-e-Qinnab," Khazaain-al-Adiva, 1911 (with English translation), 5 pages.

(56) References Cited

OTHER PUBLICATIONS

Kuhn et al., "Potent activity of carfilzomib, a novel, irreversible inhibitor of the ubiquitin-proteasome pathway, against preclinical models of multiple myeloma," Blood, 110(9):3281-3290 (2007).
Klitgaard et al., "Electrophysiological, neurochemical and regional effects of levetiracetam in the rat pilocarpine model of temporal lobe epilepsy," Seizure., 12(2):92-100, Mar. 2003.
Klitgaard et al., "Evidence for a unique profile of levetiracetam in rodent models of seizures and epilepsy." European journal of pharmacology. Jul. 24, 1998, 353(2): 191-206.
Kramer et al., "Febrile infection-related epilepsy syndrome (FIRES): pathogenesis, treatment, and outcome: a multicenter study on 77 children." Epilepsia. Nov. 2011;52(11): 1956-65. doi: 10.1111/j.1528-1167.2011.03250.x. Epub Aug. 2, 20119.
Kruk-Slomka et al., "A comparison of mecamylamine and bupropion effects on memory-related responses induced by nicotine and scopolamine in the novel object recognition test in mice," Pharmacological Reports, 66(4):638-646 (2014).
KURZ & BLASS, "Use of dronabinol (delta-9-THC) in autism: A prospective single-case-study with an early infantile autistic child," Cannabinoids, 5(4):4-6 (2010).
Kwan et al., "Definition of drug resistant epilepsy: consensus proposal by the ad hoc Task Force of the ILAE Commission on Therapeutic Strategies," Epilepsia. Jun. 2010;51(6):1069-77. doi: 10.1111/j.1528-1167.2009.02397.x. Epub Nov. 3, 2009. Erratum in: Epilepsia. Sep. 2010; 51(9):1922.
Laprarie et al., "Cannabidiol is a negative allosteric modulator of the cannabinoid CB1 receptor," British J Pharmacology, 172(20):4790-4805 (2015).
Lazzari, P. et al., "Antinociceptive activity of A9-tetrahydrocannabinol non-ionic microemulsions," International Journal of Pharmaceutics, 393:238-243 (2010).
LeafScience.com [online], "What are the Highest CBD Strains?" Oct. 15, 2014, retrieved on Feb. 16, 2017, URL www.leafscience.com/2014/10/15/highest-cbd-strains/, 2 pages.
Leo et al., "Cannabidiol and epilepsy: Rationale and therapeutic potential," Pharmacological Research, 107:85-92 (2016).
Lewis, "Mystery Mechanisms," The Scientist.com, Jul. 29, 2016, retrieved on Nov. 8, 2017, URL <https://www.the-scientist.com/?articles.view/articleNo/46688/title/Mystery-Mechanisms/>, 2 pages.
Li, C. L. et al., "The use of hypromellose in oral drug delivery," Journal of Pharmacy and Pharmacology, 57:533-546 (2005).
Lieu et al. "Assessment of self-selection bias in a pediatric unilateral hearing loss study," Otolaryngol Head Neck Surg. 142(3): 427-433 (2010).
Lindamood and Colasanti, Effects of delta 9-tetrahydrocannabinol and cannabidiol on sodium-dependent high affinity choline uptake in the rat hippocampus. J Pharmacology Experimental Therapeutics, 1980, 213(2):216-221.
Long et al., "The pharmacological actions of cannabidiol," Drugs of the Future. Jul. 2005;30(7):747-53.
Loscher and Schmidt, "Modern antiepileptic drug development has failed to deliver: ways out of the current dilemma." Epilepsia. Apr. 2011;52(4):657-78. doi: 10.1111/j.1528-1167.2011.03024.x.
Lowenstein, "Chapter 363: Seizures and Epilepsy," Diseases of the Central Nervous System, 2498-2512 (2008).
Luttjohann et al. "A revised Racine's scale for PTZ-induced seizures in rats." Physiol Behav. Dec. 7, 2009;98(5):579-86. doi: 10.1016/j.physbeh.2009.09.005.
Lutz, "On-demand activation of the endocannabinoid system in the control of neuronal excitability and epileptiform seizures." Biochem Pharmacol. Nov. 1, 2004;68(9):1691-8.
Maa et al., "The case for medical marijuana in epilepsy," Epilepsia, 55(6):783-786 (2014); doi: 10.1111/epi.12610.
Mackie, "Cannabinoid receptors as therapeutic targets," Annu Rev Pharmacol Toxicol. 2006;46: 101-22.
Majoosi et al., "Key Attributes of TKDL: Saoot Baraae Sara," Kaamil-al-Sena'ah, Central Council for Research in Unani Medicine, 2005 (with English translation), 2 pages.

Malfait et al., "The nonpsychoactive cannabis constituent cannabidiol is an oral anti-arthritic therapeutic in murine collagen-induced arthritis," PNAS, Aug. 15, 2000, 97(17):9561-9566.
Manni et al., "Obstructive Sleep Apnea in a Clinical Series of Adult Epilepsy Patients: Frequency and Features of the Comorbidity," Epilepsia, 44(6):836-840 (2003).
Manno, "Status Epilepticus: Current Treatment Strategies," The Neurohospitalist. Jan. 2011, 1(1):23-31.
Mares et al., "Electrical Stimulation-Induced Models of Seizures in Model of Seizures and Epilepsy Asla Pitkanen," Philip A. Schwartzkroin & Solomon L. Moshe (Eds.), pp. 153-159 (2004).
Martin et al., "Structure-Anticonvulsant Activity Relationships of Cannabidiol Analogs," National Institute on Drug Abuse, Research Monograph Series, 1987, 79:48-58.
Mattson et al., "Comparison of carbamazepine, phenobarbital, phenytoin, and primidone in partial and secondarily generalized tonic-clonic seizures," N. Engl. J. Med, 313(3): 145-151, Jul. 18, 1985.
Mattson et al., "Prognosis for total control of complex partial and secondary generalized tonic clonic seizures," Neurology, 47:68-76, 1996.
McCormick et al., "On the cellular and network bases of epileptic seizures," Annu Rev Physiol., 63:815- 846 (2001).
McNamara, "Chapter 19: Pharmacotherapy of the Epilepsies," Goodman & Gilman's The Pharmacological Basis of Therapeutics 11th ed., McGraw-Hill Companies, pp. 501-525 (2006).
Mechoulam et al., "Cannabidiol: An Overview of Some Pharmacological Aspects," J Clin Pharmacol, 2002, 42:11S-19S.
Mechoulam et al., "Toward drugs derived from cannabis," Naturwissenschaften. Apr. 1978; 65(4): 174-9.
Medicos [online]. "Convulsive Disorders and their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving>, 3 pages.
Merlis, "Proposal for an International Classification of the Epilepsies," Epilepsia, 11:114-119 (1970).
Miller et al., "Mapping genetic modifiers of survival in a mouse model of Dravet syndrome," Genes, Brain and Behavior, 13:163-172 (2014).
Monteagudo, E. et al., "Pharmaceutical optimization of lipid-based dosage forms for the improvement of taste-masking, chemical stability and solubilizing capacity of phenobarbital," Drug Development and Industrial Pharmacy, 40(6):783-792 (2014).
Moral et al., "Pipeline on the Move," Drugs of the Future, 39(1):49-56 (2014).
Morard et al., "Conversion to Sirolimus-Based Immunosuppression in Maintenance Liver Transplantation Patients," Liver Transplantation, 13:658-664, 2007.
Morelli et al., "The effects of cannabidiol and its synergism with bortezomib in multiple myeloma cell lines. A role for transient receptor potential Vanilloid type-2," Int J Cancer, 134(11): 2534-2546 (2014).
MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.
Nabissi et al., "Cannabinoids synergize with cafilzomib, reducing multiple myeloma cells viability and migration," Oncotarget, 7:77553 (2016), 15 pages.
Neto et al., "The role of polar phytocomplexes on anticonvulsant effects of leaf extracts of Lippia Alba (Mill.) N.E. Brown chemotypes," J. Pharm Pharmacol. 61(7):933-9 (2009).
Ng et al., "Illicit drug use and the risk of new-onset seizures." Am J Epidemiol. Jul. 1990; 132(1):47-57.
Oakley et al., "Dravet Syndrome Insights into pathophysiology and therapy from a mouse model of Dravet syndrome," Epilepsia 52(Suppl. 2):59-61 (2011).
Obay et al., "Antiepileptic effects of ghrelin on pentylenetetrazole-induced seizures in rats," Peptides. Jun. 2007;28(6): 1214-9. Epub Apr. 1, 20079.
Opponent Response to the Preliminary Opinion of the Opposition Division in European Patent No. EP2448637, dated Jun. 23, 2016, 25 pages.

(56) References Cited

OTHER PUBLICATIONS

Opponent Response dated to September the 9, Preliminary 2016, 25 Opinion pages of the Opposition Division in European Patent No. EP2448637, dated Sep. 9, 2016, 25 pages.
Opponent Response to the Written Submissions in European Patent No. EP2448637, dated Oct. 12, 2016, 18 pages.
Opponent Response to the Written Submissions in European Patent No. EP2448637, dated Oct. 20, 2016, 3 pages.
Opponent Response to the Written Submissions in European Patent No. EP2448637, dated Nov. 4, 2016, 3 pages.
Pelliccia et al., [Online], "Treatment with CBD in oily solution of drug-resistant pediatric epilepsies," 2005 Congress on Cannabis and the Cannabinoids, Leiden, The Netherlands: International Association for Cannabis as Medicine, 2005, 14, retrieved on Jun. 30, 2015, URL <http//www.cannabis-med.org/studies/ww_en_db_study_show.php?s_id=173&&search_pattern=EPILEPSY>, 2 pages, Abstract only.
Pereira et al., "Study pharmacologic of the GABAergic and glutamatergic drugs on seizures and status epilepticus induced by pilocarpine in adult Wistar rats," Neurosci Lett. Jun. 4, 2007;419(3):253-7. Epub Apr. 1, 20073.
Pertwee, "Cannabinoid receptor ligands: clinical and neuropharmacological considerations, relevant to future drug discovery and development," Expert Opin Investig Drugs. Jul. 2000;9(7): 1553-71.
Pertwee, "Chapter 3: The Pharmacology and Therapeutic Potential of Cannabidiol," Cannabinoids, Ed Vincenzo Di Marzo ed., 2004, 32-83.
Pertwee, "The diverse CB1 and CB2 receptors pharmacology of three plant cannabinoids: Alpha9 Tetrahydrocannabinol, cannabidiol and alpha9-tetrahydrocannabivarin," Br. J. Pharmacol. 153 (2): 199-215, 2008.
Petrocellis, et al., "Effects of cannabinoids and cannabinoid-enriched Cannabis extracts on TRP channels and endocannabinoid metabolic enzymes," British Journal of Pharmacology (2011) 163:1479-1494.
Physician's Desk Reference, 63rd Ed., 2009, 423-461, 2192-2194, 2639-2242, 3019-3022.
Pohl, et al. "Effects of flunarizine on Metrazol-induced seizures in developing rats," Epilepsy Res. Sep. 1987;1(5):302-5.
Poortman-Van Der Meer, "A contribution to the improvement of accuracy in the quantitation of THC," Forensic Science International, Apr. 1999, 101(1): 1-8.
Porter et al., "Randomized, multicenter, dose-ranging trial of retigabine for partial-onset seizures," Neurology, 68(15):1197-1204 (2007).
Porter et al., "Report of a parent survey of cannabidiol-enriched cannabis use in pediatric treatment-resistant epilepsy," Epilepsy Behav. Dec. 2013;29(3):574-7.
Potter, "Cannabis Horticulture," Chapter 4, Handbook of Cannabis, ed. Roger G. Pertwee, pp. 65-88 (2014).
Pouton, "Lipid formulations for oral administration of drugs: non-emulsifying, self-emulsifying and 'self-microemulsifying' drug delivery systems," Eur. J. Pharm Sci, 11(Supp. 2):S93-S98 (2000).
Press et al., "Parenteral reporting of response to oral cannabis extracts for treatment of refractory epilepsy," Epilepsy Behav, 45:49-52 (2015).
Pruitt et al., "Ethanol in Liquid Preparations Intended for Children," Pediatrics, 73(3):405-407 (1984).
Raab et al., "Multiple myeloma," Lancet, 374(9686):314-339 (2009).
RABINSKI [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani et al., "Epilepsy in Aicardi - Goutières Syndrome," Official J Eur Paediatric Neurology Society, 18:30-37 (2014).
Rauca et al., "The role of superoxide dismutase and alpha-tocopherol in the development of seizures and kindling induced by pentylenetetrazol - influence of the radical scavenger alpha-phenyl-N-tert-butyl nitrone," Brain Research, 1009(1-2):203-212 (2004).
Resstel et al. "5-HT Ia receptors are involved in the cannabidiol-induced attenuation of behavioural and cardiovascular responses to acute restraint stress in rats," Br J Pharmacol., 156(1): 181-188 (2009).
Rosenberg et al., "Cannabinoids and Epilepsy," Neurotherapeutics, 12(4):747-768 (2015).
Rosenkrantz et al., "Oral and Parenteral Formulations of Marijuana Constituents," J Pharm Sci, 61(7):1106-1112 (1972).
Rubio et al., "In vivo Experimental Models of Epilepsy," Central Nervous System Agents in Medicinal Chemistry, 10:298-309 (2010).
Russo, "Taming THC: potential cannabis synergy and phytocannabinoid-termoid entourage effects," British J. of Pharm., 163:1333-1364 (2011).
Sadanandasarma et al., "Key Attributes of TKDL: Suddha Bhanga Visista Gunah Aur Matra," Rasatarangini 11th Ed., 720-723, 1979 (with English translation), 8 pages.
SalutarisDrops.com [online], "Cannabidiol for Aicardi Syndrome," Salutaris, available on or before Oct. 2014, retrieved on Feb. 10, 2017, URL <http://web.archive.org/web/20141012220050/http://salutarisdrops.corn/cannabidiol-aicardi-syndrome/>, 3 pages.
Sander, "The epidemiology of epilepsy revisited," Curr Opin Neural, 16(2):165-170 (2003).
Sandyk et al., "Preliminary trial of cannabidiol in Huntington's Disease," Marihuana: An International Research Report, 157-162 (1988).
Sastri et al., "Key Attributes of TKDL: Vijaya Kalpah (Apasmaranasaka)," Anandakandam 1st ed., 1952, 241 (with English translation), 5 pages.
Scuderi et al., "Cannabidiol in medicine: a review of its therapeutic potential in CNS disorders," Phytother Res., 23(5):597-602 (2009).
Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.
Silva et al., "Position Statement on the Use of Medical Cannabis for the Treatment of Epilepsy in Canada," Can J. Neurol. Sci., 33:783-786 (2006).
Sperling et al., "Carisbamate as adjunctive treatment of partial onset seizures in adults in two randomized, placebo-controlled trials," Epilepsia, 51(3):333-343 (2010).
Stafstrom et al., "Models of Pediatric Epilepsies: Strategies and Opportunities," Epilepsia, 47(8):1407-1414 (2006).
Stephenson, "In Memoriam: Professor Jean Aicardi (1926-2015)," Pediatric Neurology, 54:3-4 (2016).
Stott et al., "Cannabinoids for the pharmaceutical industry," Euphytica, 140:83-93 (2004).
Strickley, "Solubilizing Excipients in Oral and Injectable Formulations," Table VIII, Pharmaceutical Research, 21(2):201-230 (2004).
Swann et al., "The effects of seizures on the connectivity and circuitry of the developing brain," Ment Retard Dev Disabil Res Rev., 10(2):96-100 (2004).
Thomas et al., "Evidence that the plant cannabinoid Delta9-tetrahydrocannabivarin is a cannabinoid CBI and CB2 receptor antagonist," Br J Pharmacol., 146(7):917-926 (2005).
Thomas et al., "Cannabidiol displays unexpectedly high potency as an antagonist of CB1 and CB2 receptor agonists in vitro," British J Pharmacology, 150(5):613-623 (1988).
Thumma et al., "Influence of plasticizers on the stability and release of a prodrug of 19-tetrahydrocannabinol incorporated in poly (ethylene oxide) matrices," Eur J Pharmaceutics and Biopharmaceutics, 70(2):605-614 (2008).
Thurman et al., "Standards for epidemiologic studies and surveillance of epilepsy," Epilepsia, 52 (Suppl 7):2-26 (2011).
Thurston, "Avoid Charlotte's Web for Epilepsy," Jun. 26, 2014, URL <http://drthurstone.com/charlotted-web-not-safest-option-epilepsy-treatment/>, 4 pages.
Trembly & Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract only.
Turkanis et al., "An Electrophysiological Analysis of the Anticonvulsant Action of Cannabidiol on Limbic Seizures in Conscious Rats," Epilepsia., 20:351-363 (1979).

(56) References Cited

OTHER PUBLICATIONS

Unimed Pharmaceuticals, Inc., "Marinol®," Jul. 2006, <https://www.accessdata.fda.gov/drugsatfda docs/label/2006/018651s025s026lbl.pdf>, 11 pages.
FDA Guidance for Industry: Estimating the Maximum Safe Starting Dose in Initial Clinical Trials for Therapeutics in Adult Healthy Volunteers, U.S. Department of Health and Human Services, Food and Drug Administration Center for Drug Evaluation and Research (CDER), Jul. 2005, 30 pages.
Usami et al., "Synthesis and pharmacological evaluation in mice of halogenated cannabidiol derivatives," Chem Pharm Bull (Tokyo), 47(11): 1641-1645 (1999).
USPTO Decision on Appeal in U.S. Appl. No. 10/318,659 (Appeal 2009-011751), dated Jul. 8, 2010, 23 pages.
USPTO Decision on Appeal in U.S. Appl. No. 13/698,730 (Appeal 2016-006358), dated Jun. 21, 2017, 6 pages.
USPTO Information Disclosure Statement Form PTO-1449 for U.S. Appl. No. 13/380,305, dated Nov. 24, 2014, 8 pages.
USPTO Notice of Allowance in U.S. Appl. No. 13/380,305, dated Dec. 10, 2014, 5 pages.
USPTO Notice of Allowance in U.S. Appl. No. 13/380,305, dated Mar. 19, 2015, 7 pages.
USPTO Notice of Allowance in U.S. Appl. No. 13/380,305, dated Aug. 25, 2014, 6 pages.
USPTO Request for Continued Examination with Amendment and Information Disclosure Statement in U.S. Appl. No. 13/380,305, filed Mar. 2, 2015, 8 pages.
USPTO Third Preliminary Amendment in U.S. Appl. No. 13/380,305, dated May 23, 2014, 4 pages.
Utah.gov [online], "2nd Agenda Controlled Substances Advisory Committee Meeting," Nov. 12, 2013, URL <https://www.utah.gov/pmn/files/81459.pdf>, 63 pages.
Van Rijckevorsel, "Treatment of Lennox-Gastaut Syndrome: overview and recent findings," Neuropsychiatr Dis Treat, 4(6): 1001-1019 (2008).
Velasco et al., "Anticancer mechanisms of cannabinoids," Curr Oncol, 23(2):S23-S32 (2016).
Velisek, "Chapter 11: Models of Chemically-Induced Acute Seizures," Models of Seizures and Epilepsy, pp. 127-152 (2006).
Veliskova, "Chapter 48: Behavioral Characterization of Seizures in Rats," Models of Seizures and Epilepsy, pp. 601-611 (2006).
Vollner et al., "Haschisch XX+[Haschisc XX+]: Cannabidivarin, a new hashish substance," Tetrahedron Letters, 10(3):145-147 (1969).
Wahle et al., "Development of Tolerance to the Anticonvulsant Effect of Valproate but not to Ethosuximide in a Rat Model of Absence Epilepsy," Eur J Pharma, 181(1-2): 1-8 (1990).
Wallace et al., "Pharmacotherapy for Dravet Syndrome," Pediatr. Drugs, 18:197-208 (2016).
Wallace et al., "Assessment of the role of CB 1 receptors in cannabinoid anticonvulsant effects," Eur J Pharmacol., 428(1):51-57 (2001).
Weston et al., "Tetrahydrocannabivarin exhibits anticonvulsant effects in a piriform cortical brain slice model of epileptiform activity," Proceedings of the British Pharm Society, Dec. 2006, retrieved on Mar. 1, 2017, URL <http://www.pA2online.org/abstrat/abstract.jsp?abid=28533>, 1 page, Abstract only.
Wikipedia.org [online], "Cannabinoid," Wikipedia, Apr. 2003, retrieved on Mar. 1, 2017, URL <https://en.wikipedia.org/wiki/Cannabinoid>, 15 pages.
Wingerchuk, "Cannabis for medical purposes: cultivating science, weeding out the fiction," Lancet, 364:315-316 (2004).
Yu et al., "Reduced sodium current in GABAergic interneurons in a mouse model of severe myoclonic epilepsy in infancy," Nature Neuroscience, 9(9): 1142-1149 (2006).
Yuriev, "Endogenic cannabinoid system is a new perspective object of pharmacotherapeutic effect to disease of nervous system," Ukrainsky Mnemotechny Chasopis, 6(50):21-29 (2005) (with English Abstract).
Zamberletti et al., "Alterations of prefrontal cortex GABAergic transmission in the complex psychotic-like phenotype induced by adolescent delta-9-tetrahydrocannabinol exposure in rats," Neurobiology of Disease, 63:35-47 (2014).
Zhao et al., "Chapter 27: Repetitive Seizures in the Immature Brain," Models of Seizures and E[epilepsy, 341-350 (2006).
Zhornitsky & Potvin, "Cannabidiol in Humans—The Quest for Therapeutic Targets," Pharmaceuticals, 5:529-552 (2012).
Zuardi et al., "Cannabidiol, a Cannabis sativa constituent, as an antipsychotic drug," Braz J Med Biol Res., 39(4):421-429 (2006).
Zuardi et al., "Cannabidiol: from an inactive cannabinoid to a drug with wide spectrum of action," Rev Bras Psiquiatr, 30(3):271-280 (2008).
U.S. Appl. No. 15/640,033, filed Jun. 30, 2017.
U.S. Appl. No. 16/768,241, filed May 29, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 16/935,005, filed Jul. 21, 2020.
U.S. Appl. No. 17/012,448, filed Sep. 4, 2020.
U.S. Appl. No. 17/050,956, filed Oct. 27, 2020.
U.S. Appl. No. 17/102,109, filed Nov. 23, 2020.
U.S. Appl. No. 17/231,625, filed Apr. 15, 2021.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/472,000, filed Sep. 10, 2021.
U.S. Appl. No. 17/548,232, filed Dec. 10, 2021.
U.S. Appl. No. 17/606,370, filed Oct. 25, 2021.
U.S. Appl. No. 17/611,824, filed Nov. 16, 2021.
U.S. Appl. No. 17/529,005, filed Nov. 17, 2021.
U.S. Appl. No. 17/552,487, filed Dec. 16, 2021.
U.S. Appl. No. 17/576,868, filed Jan. 14, 2022.
U.S. Appl. No. 17/585,485, filed Jan. 26, 2022.
U.S. Appl. No. 17/627,946, filed Jan. 18, 2022.
U.S. Appl. No. 17/631,069, filed Jan. 28, 2022.
U.S. Appl. No. 17/638,629, filed Feb. 25, 2022.
U.S. Appl. No. 17/689,607, filed Mar. 8, 2022.
U.S. Appl. No. 17/744,224, filed May 13, 2022.
U.S. Appl. No. 17/705,443, filed Mar. 28, 2022.
U.S. Appl. No. 17/768,048, filed Apr. 11, 2022.
U.S. Appl. No. 17/770,435, filed Apr. 20, 2022.
U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.
U.S. Appl. No. 17/777,734, filed May 18, 2022.
U.S. Appl. No. 17/777,677, filed May 18, 2022.
U.S. Appl. No. 17/777,681, filed May 18, 2022.
U.S. Appl. No. 17/841,167, filed Jun. 15, 2022.
U.S. Appl. No. 17/786,949, filed Jun. 17, 2022.
U.S. Appl. No. 17/817,753, filed Aug. 5, 2022.
U.S. Appl. No. 17/853,367, filed Jun. 29, 2022.
U.S. Appl. No. 18/002,437, filed Dec. 19, 2022.
U.S. Appl. No. 18/005,838, filed Jan. 17, 2023.
U.S. Appl. No. 18/005,841, filed Jan. 17, 2023.
U.S. Appl. No. 18/005,845, filed Jan. 17, 2023.
U.S. Appl. No. 18/005,843, filed Jan. 17, 2023.
U.S. Appl. No. 18/005,847, filed Jan. 17, 2023.
U.S. Appl. No. 18/005,848, filed Jan. 17, 2023.
U.S. Appl. No. 18/005,851, filed Jan. 18, 2023.
U.S. Appl. No. 18/005,852, filed Jan. 18, 2023.
U.S. Appl. No. 18/005,853, filed Jan. 18, 2023.
U.S. Appl. No. 18/005,959, filed Jan. 18, 2023.
U.S. Appl. No. 18/005,960, filed Jan. 18, 2023.
U.S. Appl. No. 18/005,961, filed Jan. 18, 2023.
U.S. Appl. No. 18/006,125, filed Jan. 19, 2023.
U.S. Appl. No. 18/006,127, filed Jan. 19, 2023.
U.S. Appl. No. 18/006,129, filed Jan. 19, 2023.
U.S. Appl. No. 18/006,131, filed Jan. 19, 2023.
U.S. Appl. No. 18/006,133, filed Jan. 19, 2023.

(56) References Cited

OTHER PUBLICATIONS

U.S. Appl. No. 18/006,121, filed Jan. 19, 2023.
U.S. Appl. No. 18/161,603, filed Jan. 30, 2023.
U.S. Appl. No. 18/170,235, filed Feb. 16, 2023.
U.S. Appl. No. 18/043,810, filed Mar. 2, 2023.
U.S. Appl. No. 18/044,941, filed Mar. 10, 2023.
U.S. Appl. No. 18/245,856, filed Mar. 17, 2023.
U.S. Appl. No. 18/186,792, filed Mar. 20, 2023.
U.S. Appl. No. 18/311,221, filed May 2, 2023.
U.S. Appl. No. 18/320,906, filed May 19, 2023.
U.S. Appl. No. 18/256,307, filed Jun. 7, 2023.
U.S. Appl. No. 18/257,373, filed Jun. 14, 2023.
U.S. Appl. No. 18/257,537, filed Jun. 14, 2023.
U.S. Appl. No. 18/257,479, filed Jun. 14, 2023.
U.S. Appl. No. 18/258,485, filed Jun. 20, 2023.
U.S. Appl. No. 18/446,405, filed Aug. 8, 2023.
U.S. Appl. No. 18/546,254, filed Aug. 11, 2023.
U.S. Appl. No. 18/548,003, filed Aug. 25, 2023.
U.S. Appl. No. 18/477,467, filed Sep. 28, 2023.
U.S. Appl. No. 18/479,671, filed Oct. 2, 2023.
Eloy et al., "Solid dispersions containing ursolic acid in Poloxamer 407 and PEG 6000: A comparative study of fusion and solvent methods," Powder Technology, 253:98-106 (2014).
Guidance for Industry on Botanical Drug Products; Availability, U.S. Department of Health and Human Services, Food and Drug Administration, 69 FR 32359, Aug. 2000; https://www.federalregister.gov/documents/2004/06/09/04-13031/guidance-for-industry-on-botanical-drug-products-availability, 2 pages.
[No. Author Listed] Poloxamer. file:///C:/Users/lmattison/Desktop/poloxamer%20cannabis/Poloxamer.pdf. Published: Nov. 6, 2022; 4 pages.

\* cited by examiner

ORAL CANNABINOID FORMULATIONS

CROSS-REFERENCE TO RELATED APPLICATIONS

This application is a divisional of U.S. patent application Ser. No. 16/314,569, filed Dec. 31, 2018, which claims the benefit of International PCT Application No. PCT/GB2017/051914, filed Jun. 29, 2017; and Great Britain Application No. 1611547.9, filed Jul. 1, 2016; each of the aforementioned applications are incorporated herein by reference in its entirety.

The present invention relates to a cannabinoid containing oral solution.

BACKGROUND TO THE INVENTION

The use of cannabinoids in medicine has necessitated finding more effective ways of drug delivery. This is in part due to factors such as, poor aqueous solubility, limited bioavailability, and cannabinoid instability, but the use of cannabinoids at relatively high doses (in daily amounts of up to 2000 mg) and/or in challenging patient groups, e.g. young children, and/or for particular indications, can create additional challenges.

There are currently three commercially available cannabinoid formulations on the market.

Dronabinol (Marinol®) is a synthetic tetrahydrocannabinol (THC) which is delivered orally, in sesame oil as capsules.

Nabilone (Cesamet®) is a synthetic cannabinoid and an analog of THC and is delivered orally in capsules with povidone and corn starch.

Nabiximols (Sativex®) is a natural extract of cannabinoids containing defined amounts of THC and Cannabidiol (CBD) and is delivered as a liquid, by way of an oromucosal spray.

The applicant also provides an oral solution containing CBD (Epidiolex®) on a named patient basis. The CBD is formulated in sesame seed oil and further comprises the sweetener sucralose (600× the sweetness intensity of sucrose), strawberry flavouring and up to 10% v/v ethanol.

Whilst there is no clear FDA guidance for maximum allowable ethanol concentration in prescription medicines, an article (Ethanol in Liquid Preparations Intended for Children, Paediatrics: Official Journal of The American Academy of Paediatrics, 1984: 73:405), recommends that a Blood Alcohol Concentration (BAC) of 0.25 g/L (250 mg/L) should not be exceeded following a single dose of alcohol containing medications.

WO 2015/184127 (Insys) discloses a number of different oral formulations including: an alcohol free formulation in which the cannabinoid is formulated in a mix of polyethylene glycol and propylene glycol, optionally with water, a formulation containing alcohol and a formulation containing lipids. In each of the formulations disclosed, the cannabinoid is a synthetically produced (as opposed to a naturally extracted) cannabidiol.

The specification teaches the inclusion of a number of pharmaceutically acceptable excipients such as, anti-oxidants, sweeteners, enhancers, preservatives, flavouring agents and pH modifiers.

According to European Medicine Agency draft guideline (EMA/CHMP/507988/2013), for 2 to 6 years old children, a theoretical limit for Blood Alcohol Concentration (BAC) following single administration of a formulation containing alcohol is not more than 0.01 g/L (10 mg/L) and ethanol intake should be not more than 6 mg/kg/day.

For paediatric products aimed at younger children, it is desirable to have low or no ethanol formulations, preferably dispensed as syrup, as younger children find it difficult to swallow capsules. They also favour sweet, flavoured products, particularly where the taste of cannabinoid requires masking.

A problem with the use of pharmaceutically acceptable sweeteners, and flavouring agents is that they are generally polar in nature, and thus unlike the cannabinoids which are highly lipophilic, they require a polar solvent to dissolve them.

An object of the present invention was to develop a lipid based oral formulation which contained less than 10% (v/v) ethanol, which was palatable, and could be delivered to young children as syrup, in relatively small volumes, typically less than 10 ml.

BRIEF SUMMARY OF THE DISCLOSURE

In accordance with a first aspect of the present invention there is provided a cannabinoid containing oral solution comprising: a cannabinoid, a lipid solvent, a sweetener and ethanol, characterised in that the sweetener is an ultrahigh potency sweetener.

An ultrahigh potency sweetener is defined herein as a sweetener with a sweetness intensity compared to sucrose of greater than 750.

Preferably the ultrahigh potency sweetener has a sweetness intensity compared to sucrose of greater than 1000, more preferably greater than 5000.

In one embodiment of the invention the ultrahigh potency sweetener is (N—[N-(3,3-dimethylbutyl)-L-α-aspartyl]-L-phenylalanine 1-methyl ester) (Neotame).

In a further embodiment the ultrahigh potency sweetener is N—[N-3-(3-hydroxy-4-methoxyphenyl)propyl-α-L-aspartyl]-L-phenylalanine 1-methyl ester) (Advantame).

Preferably the cannabinoid containing oral solution further comprises a flavourant.

Preferably the cannabinoid is selected from: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA). More preferably the cannabinoid is CBD.

It is preferred that the cannabinoid containing oral solution has a cannabinoid present in an amount of from 5 to 40% (w/v), ethanol present in an amount of less than 2% (w/v), ultrahigh potency sweetener present in less than 0.05% (w/v) flavourant, more preferably still less than 0.01% (w/v) flavourant present in an amount of less 0.2% (w/v) and lipid solvent present q.s. to 100%.

More preferably the cannabinoid is CBD, the ultrahigh potency sweetener is Neotame, the flavourant is strawberry flavour and the lipid solvent is sesame oil.

Preferably the cannabinoid containing oral solution is stable in climatic zones I and II for up to 24 months at 25° C. or is stable in climatic zones III and IV for up to 18 months at 30° C.

Surprisingly, the formulations of the invention were stable without the need for the incorporation of stability enhancers such as anti-oxidants or complexing agents.

Preferably the cannabinoid containing oral solution is absent of a stabilizing agent.

More preferably the stabilizing agent which the cannabinoid containing oral solution is absent of is an antioxidant or a chelating agent.

The formulation may be packaged for use in a bottle, oral or enteral syringe, metered dose device or other container used to store or administer liquid oral medications.

In accordance with a second aspect of the present invention there is provided a method of treating a subject comprising administering a cannabinoid containing oral solution.

Preferably the subject is a human.

Preferably the cannabinoid containing oral solution is for use in the treatment of epilepsy and syndromes associated therewith, Dravet Syndrome, Lennox Gastaut Syndrome, myoclonic seizures, juvenile mycolonic epilepsy, refractory epilepsy, schizophrenia, juvenile spasms, West syndrome, infantile spasms, refractory infantile spasms, tuberous sclerosis complex, brain tumors, neuropathic pain, cannabis use disorder, post-traumatic stress disorder, anxiety, early psychosis, Alzheimer's Disease, and autism.

In accordance with a third aspect of the present invention there is provided a cannabinoid containing oral solution for use in the treatment of a disease or disorder selected from the group consisting of epilepsy and syndromes associated therewith, Dravet Syndrome, Lennox Gastaut Syndrome, myoclonic seizures, juvenile mycolonic epilepsy, refractory epilepsy, schizophrenia, juvenile spasms, West syndrome, infantile spasms, refractory infantile spasms, tuberous sclerosis complex, brain tumors, neuropathic pain, cannabis use disorder, post-traumatic stress disorder, anxiety, early psychosis, Alzheimer's Disease, and autism.

DETAILED DESCRIPTION

The Applicant initially sought to replace the ethanol in their oral lipid formulation with an alternative pharmaceutically acceptable solvent, such as propylene glycol, polyethylene glycol or glycerin but found their miscibility with sesame oil, across a range of concentrations (0.5-10%) tested, was not satisfactory.

They then looked at substituting the sweetener they used, sucralose, with an alternative pharmaceutically acceptable sweetener, such as, for example, sucrose, aspartame, saccharin, dextrose, mannitol or xylitol without success due to for example, taste profile or physical stability.

When these two approaches failed they, unconventionally, tried ultrahigh potency sweeteners, which whilst approved by the FDA in foods, are not generally considered as sweeteners for use in pharmaceuticals. The two tested, Advantame and Neotame proved surprisingly effective and formulations containing these sweeteners did not require stabilizing with anti-oxidants and chelating agents as is common in cannabinoid containing formulations. The Examples that follow describe the development of the claimed formulations which show good stability.

Example 1—Selection of Alternative Sweeteners

Alternative sweeteners to sucralose (comparator) were selected as shown in Table 1 below.

TABLE 1

| Sweetener | Acceptable Daily Intake (mg/kg/day)* | Multiplier of Sweetness Intensity Compared to Table Sugar (Sucrose) |
|---|---|---|
| Sucralose | 5 | 600× |
| Saccharin | 15 | 200-700× |
| Saccharin Dihydrate | 15 | 200-700× |
| Aspartame | 50 | 200× |
| Neotame | 0.3 | 7,000-13,000× |
| Advantame | 32.8 | 20,000× |

*Acceptable daily intake values derived from FDA website: http://www.fda.gov/Food/IngredientsPackagingLabeling/FoodAdditivesIngredients/ucm397725.htm#SummaryTable Batches using these sweeteners were prepared as shown in Table 2 below, with the concentrations of each sweetener being selected based on its relative sweetness compared to sucralose.

TABLE 2

| Ingredients | Batch ET03/049C | Batch ET03/049D | Batch ET03/049A | Batch ET03/049B | Batch ET03/012I |
|---|---|---|---|---|---|
| Saccharin | 0.05% w/v | — | — | — | — |
| Saccharin Dihydrate | — | 0.05% w/v | — | — | — |
| Aspartame | — | — | 0.15% w/v | — | — |
| Neotame | — | — | — | 0.005% w/v | — |
| Advantame | — | — | — | — | 0.0025% w/v |
| Anhydrous Ethanol | 10% v/v | 10% v/v | 10% v/v | 10% v/v | 2% v/v |
| Strawberry Flavour | 0.10% w/v | 0.10% w/v | 0.10% w/v | 0.10% w/v | 0.10% w/v |
| Refined Sesame Oil | q.s. to 100% | q.s. to 100% | q.s. to 100% | q.s. to 100% | q.s. to 100% |

Four of the five formulations were clear solutions with the exception of Aspartame which did not completely solubilise in ethanol.

The Formulations made with Saccharin and Saccharin dihydrate produced an unpleasant taste, and also had a lingering bitter after taste.

On the other hand, the Formulations made with Neotame and Advantame both had a good taste profile, with no bitter after taste.

Therefore Neotame and Advantame were both considered suitable candidates for further development.

Example 2—Evaluation of an Advantame Formulation

An experiment (ET03/015) was carried out to determine the lowest ethanol concentration required to solubilise Advantame. Table 3 details the batches made with various ethanol concentrations ranging from 0.5% to 3.0% v/v.

TABLE 3

| Ingredients | Batch ET03/015 A | Batch ET03/015 B | Batch ET03/015 C | Batch ET03/015 D | Batch ET03/015 E | Batch ET03/015 F |
|---|---|---|---|---|---|---|
| Advantame | | | 0.0025% w/v | | | |
| Strawberry Flavour | | | 0.10% w/v | | | |
| Anhydrous Ethanol | 0.5% v/v | 1.0% v/v | 1.5% v/v | 2.0% v/v | 2.5% v/v | 3.0% v/v |
| Refined Sesame Oil | | | q.s. to 100% | | | |

These batches were stored at 25° C./60% RH and 40° C./75% RH for up to 4 weeks and observed for any signs of precipitation. There was no precipitation observed over the period assessed. Therefore it was concluded that Advantame can be used as a sweetener and can be solubilised at ethanol concentration of at least as low as 0.5% v/v. i.e. the concentration of ethanol required in the formulation can be reduced by a factor of 20 compared to a sucralose containing formulation.

Example 3—Preparation of Neotame Formulations

In an experiment (ET03/127), various formulations were prepared with different levels of CBD (25 mg/ml, 100 mg/ml and 200 mg/ml), Neotame (0.005 and 0.01% w/v) and ethanol (0.5 to 3.0% v/v).

The objective of the experiment was to determine the physical stability of the formulations with different concentrations of CBD, Neotame and ethanol. Tables 4 to 6 below detail the compositions of the formulations.

TABLE 4

(CBD 25 mg/ml)

| Ingredients | Batch A/25 | Batch B/25 | Batch C/25 | Batch D/25 | Batch E/25 | Batch F/25 | Batch G/25 | Batch H/25 |
|---|---|---|---|---|---|---|---|---|
| Cannabidiol | | | | 2.5% w/v | | | | |
| Neotame | 0.005% w/v | 0.01% w/v | 0.005% w/v | 0.01% w/v | 0.005% w/v | 0.01% w/v | 0.005% w/v | 0.01% w/v |
| Anhydrous Ethanol | 0.5% v/v | 0.5% v/v | 1.0% v/v | 1.0% v/v | 2.0% v/v | 2.0% v/v | 3.0% v/v | 3.0% v/v |
| Flavour | | | | 0.10% w/v | | | | |
| | | | | q.s. to 100% | | | | |

TABLE 5

(CBD 100 mg/ml)

| Ingredients | Batch A/100 | Batch B/100 | Batch C/100 | Batch D/100 | Batch E/100 | Batch F/100 | Batch G/100 | Batch H/100 |
|---|---|---|---|---|---|---|---|---|
| Cannabidiol | | | | 10.0% w/v | | | | |
| Neotame | 0.005% w/v | 0.01% w/v | 0.005% w/v | 0.01% w/v | 0.005% w/v | 0.01% w/v | 0.005% w/v | 0.01% w/v |
| Anhydrous Ethanol | 0.5% v/v | 0.5% v/v | 1.0% v/v | 1.0% v/v | 2.0% v/v | 2.0% v/v | 3.0% v/v | 3.0% v/v |
| Flavour | | | | 0.10% w/v | | | | |
| Refined Sesame Oil | | | | q.s. to 100% | | | | |

TABLE 6

(CBD 200 mg/ml)

| Ingredients | Batch A/200 | Batch B/200 | Batch C/200 | Batch D/200 | Batch E/200 | Batch F/200 | Batch G/200 | Batch H/200 |
|---|---|---|---|---|---|---|---|---|
| Cannabidiol | | | | 20.0% w/v | | | | |
| Neotame | 0.005% w/v | 0.01% w/v | 0.005% w/v | 0.01% w/v | 0.005% w/v | 0.01% w/v | 0.005% w/v | 0.01% w/v |
| Anhydrous Ethanol | 0.5% v/v | 0.5% v/v | 1.0% v/v | 1.0% v/v | 2.0% v/v | 2.0% v/v | 3.0% v/v | 3.0% v/v |
| Flavour | | | | 0.10% w/v | | | | |
| Refined Sesame Oil | | | | q.s. to 100% | | | | |

Example 4—Testing of Neotame Formulations for Physical Stability

The 25 mg/ml and 100 mg/ml batches were tested for physical stability by opening the bottles and allowing them to stand for 2 weeks to let the ethanol evaporate. This was done as a worst case in-use scenario where the bottle is repeatedly opened and closed multiple times during use. The batches were monitored for any signs of precipitation and the ethanol content measured. The results are provided in Table 7.

TABLE 7

| Batch | CBD Assay (mg/ml) Initial | Appearance of Solution Initial | Appearance of Solution Day 14 | Ethanol Content (% v/v) Target | Ethanol Content (% v/v) Initial | Ethanol Content (% v/v) Day 14 |
|---|---|---|---|---|---|---|
| A/25 | 24.6 | Clear | Clear | 0.5 | 0.6 | 0.03 |
| B/25 | 24.6 | Clear | Clear | 0.5 | 0.6 | 0.02 |
| C/25 | 24.9 | Clear | Clear | 1.0 | 1.1 | 0.04 |
| D/25 | 24.4 | Clear | Clear | 1.0 | 1.0 | 0.05 |
| E/25 | 24.3 | Clear | Clear | 2.0 | 2.0 | 0.09 |
| F/25 | 24.8 | Clear | Clear | 2.0 | 2.1 | 0.14 |
| G/25 | 24.3 | Clear | Clear | 3.0 | 3.4 | 0.14 |
| H/25 | 24.3 | Clear | Clear | 3.0 | 3.0 | 0.12 |
| A/100 | 98.9 | Clear | Clear | 0.5 | 0.6 | 0.04 |
| B/100 | 99.2 | Clear | Clear | 0.5 | 0.7 | 0.05 |
| C/100 | 100.0 | Clear | Clear | 1.0 | 1.2 | 0.10 |
| D/100 | 100.1 | Clear | Clear | 1.0 | 1.1 | 0.15 |
| E/100 | 100.1 | Clear | Clear | 2.0 | 2.1 | 0.20 |
| F/100 | 97.4 | Clear | Clear | 2.0 | 2.1 | 0.18 |
| G/100 | 99.9 | Clear | Clear | 3.0 | 3.3 | 0.25 |
| H/100 | 100.4 | Clear | Clear | 3.0 | 3.3 | 0.29 |

All 25 mg/ml and 100 mg/ml batches were clear without any signs of precipitation. The ethanol content dropped significantly at day 14 for all batches; however there were no signs of precipitation of Neotame even after the ethanol content had dropped by more than 85% of its initial concentration. This indicates that Neotame can be physically solubilised at concentrations up to 0.01% w/v in ethanol.

As Neotame is freely soluble in ethanol at room temperature only a small quantity of ethanol is required to keep Neotame solubilised in the formulation. Accordingly it was decided to use Neotame in a formulation at 0.008% w/v concentration for optimum sweetness with ethanol at a concentration of 1% v/v (0.79% w/v).

Example 5—Long Term Stability Testing 100 mg/ml and 200 mg/ml formulations were made up as per Table 8 below>

TABLE 8

| Component | Function | Reference to Quality standard | Quantitative Composition CBD 100 mg/ml oral solution | Quantitative Composition CBD 200 mg/ml oral solution |
|---|---|---|---|---|
| Cannabidiol | Active | In-house | 10.0% w/v | 20.0% w/v |
| Anhydrous Ethanol | Sweetener solubilizer | Ph Eur & USP/NF | 0.79% w/v[†] | 0.79% w/v[†] |
| Neotame | Sweetener | USP/NF | 0.008% w/v | 0.008% w/v |
| Strawberry Flavour | Flavour | In-house | 0.10% w/v | 0.10% w/v |
| Refined Sesame Oil | Solubilizer | Ph Eur & USP/NF | q.s. to 100% | q.s. to 100% |

Note:
[†]0.79% w/v is equivalent to 1% v/v of anhydrous ethanol

The method of manufacture comprised solubilising the CBD in sesame oil. The sweetener and flavour were mixed in ethanol and the ethanolic phase was then mixed with the sesame oil phase containing dissolved CBD.

The long term stability testing was according to ICH guideline (http://www.ich.org/fileadmin/Public_Web_Site/ICH_Products/Guidelines/Quality/Q1A_R2/Step4/Q1A_R2_Guideline.pdf) with different CBD strengths as detailed in Table 9 below.

TABLE 9

| Study Reference | Description | Formula Ingredients | Formula Composition | Storage Conditions |
|---|---|---|---|---|
| DSP-15-10-02 | CBD 100 mg/ml oral solution | CBD | 10.0% w/v | 25° C./60% RH |
| | | Anhydrous Ethanol | 0.79% w/v | 30° C./65% RH |
| | | Neotame | 0.008% w/v | 40° C./75% RH |
| | | Strawberry Flavour | 0.10% w/v | |
| | | Refined Sesame Oil | q.s. to 100% | |

TABLE 9-continued

| Study Reference | Description | Ingredients | Composition | Storage Conditions |
|---|---|---|---|---|
| | CBD 200 mg/ml oral solution | CBD<br>Anhydrous Ethanol<br>Neotame<br>Strawberry Flavour<br>Refined Sesame Oil | 20.0% w/v<br>0.79% w/v<br>0.008% w/v<br>0.10% w/v<br>q.s. to 100% | 25° C./60% RH<br>30° C./65% RH<br>40° C./75% RH |

The tests shown in Table 10 below were used to determine the stability of the formulations.

TABLE 10

| Test | Test method |
|---|---|
| Appearance of Solution | Visual check |
| CBD Content | Ultra-Performance Liquid Chromatography (UPLC) |
| Degradants: | |
| CBE I | |
| CBE II | |
| OH-CBD | |
| Total Degradants | |
| Microbial: | Pharmacopoeial |
| TAMC | |
| TYMC | |
| E. coli | |

The results from illustrated in Tables 11 to 15 for the 100 mg/ml CBD formulation and 16 to 20 for the 200 mg/ml CBD formulation.

TABLE 11

Stability data for CBD 100 mg/ml Oral Solution Batch ET04/126-B 25° C. ± 2° C./60% RH ± 5% RH, Vertical

| Test | Specification | Time-point (months) | | | |
|---|---|---|---|---|---|
| | | 0 | 2 | 3 | 6 |
| Appearance of Solution | A clear, colorless to yellow solution | A clear solution free from visible particulates | A clear solution free from visible particulates | A clear solution free from visible particulates | A clear solution free from visible particulates |
| CBD Content | 90.0-110.0 mg/ml (90.0-110.0% LC) | 99.5 mg/ml (99.5%) | 101.3 mg/ml (101.3%) | 99.9 mg/ml (99.9%) | 98.9 mg/ml (98.9%) |
| Degradants | | | | | |
| CBE I | NMT 0.2% | ND | ND | ND | ND |
| CBE II | NMT 0.2% | ND | ND | ND | ND |
| OH-CBD | NMT 0.2% | 0.03% | ND | 0.02% | 0.05% |
| Total Degradants | NMT 1.0% | 0.03% | ND | 0.02% | 0.05% |
| Microbial: | | | | | |
| TAMC | NMT $10^3$ cfu/g | Complies with pharmacopoeial requirements | Complies with pharmacopoeial requirements | Complies with pharmacopoeial requirements | Complies with pharmacopoeial requirements |
| TYMC | NMT $10^2$ cfu/g | | | | |
| E. coli | Absent in 1 g | | | | |

ND = Not Detected

TABLE 12

Stability data for CBD 100 mg/ml Oral Solution Batch ET04/126-B 30° C. ± 2° C./65% RH ± 5% RH, Vertical

| Test | Specification | Time-point (months) | | | |
|---|---|---|---|---|---|
| | | 0 | 2 | 3 | 6 |
| Appearance of Solution | A clear, colorless to yellow solution | A clear solution free from visible particulates | A clear solution free from visible particulates | A clear solution free from visible particulates | A clear solution free from visible particulates |
| CBD Content | 90.0-110.0 mg/ml (90.0-110.0% LC) | 99.5 mg/ml (99.5%) | 100.8 mg/ml (100.8%) | 99.1 mg/ml (99.1%) | 99.0 mg/ml (99.0%) |

TABLE 12-continued

Stability data for CBD 100 mg/ml Oral Solution Batch ET04/126-B 30° C. ± 2° C./65% RH ± 5% RH, Vertical

| | | Time-point (months) | | | |
|---|---|---|---|---|---|
| Test | Specification | 0 | 2 | 3 | 6 |
| Degradants: | | | | | |
| CBE I | NMT 0.2% | ND | ND | ND | ND |
| CBE II | NMT 0.2% | ND | ND | ND | ND |
| OH-CBD | NMT 0.2% | 0.03% | ND | 0.02% | 0.05% |
| Total Degradants | NMT 1.0% | 0.03% | ND | 0.02% | 0.05% |
| Microbial: | | | | | |
| TAMC | NMT $10^3$ cfu/g | Complies with pharmacopoeial requirements | Complies with pharmacopoeial requirements | Complies with pharmacopoeial requirements | Complies with pharmacopoeial requirements |
| TYMC | NMT $10^2$ cfu/g | | | | |
| E. coli | Absent in 1 g | | | | |

ND = Not Detected

TABLE 13

Stability data for CBD 100 mg/ml Oral Solution Batch ET04/126-B 40° C. ± 2° C./75% RH ± 5% RH, Vertical

| | | Time-point (months) | | |
|---|---|---|---|---|
| Test | Specification | 0 | 2 | 6 |
| Appearance of Solution | A clear, colorless to yellow solution | A clear solution free from visible particulates | A clear solution free from visible particulates | A clear solution free from visible particulates |
| CBD Content | 90.0-110.0 mg/ml (90.0-110.0% LC) | 99.5 mg/ml (99.5%) | 100.8 mg/ml (100.8%) | 98.8 mg/ml (98.8%) |
| Degradants | | | | |
| CBE I | NMT 0.2% | ND | ND | 0.05% |
| CBE II | NMT 0.2% | ND | ND | ND |
| OH-CBD | NMT 0.2% | 0.03% | ND | 0.06% |
| Total Degradants | NMT 1.0% | 0.03% | ND | 0.11% |
| Microbial: | | | | |
| TAMC | NMT $10^3$ cfu/g | Complies with pharmacopoeial requirements | Complies with pharmacopoeial requirements | Complies with pharmacopoeial requirements |
| TYMC | NMT $10^2$ cfu/g | | | |
| E. coli | Absent in 1 g | | | |

ND = Not Detected

TABLE 14

Stability data for CBD 100 mg/ml Oral Solution Batch ET04/126-B In-Use 25° C. ± 2° C./60% RH ± 5% RH, Vertical

| Test | Specification | Time-point (Initial) 8 weeks |
|---|---|---|
| Appearance of Solution | A clear, colorless to yellow solution | A clear solution free from visible particulates |
| CBD Content | 90.0-110.0 mg/ml (90.0-110.0% LC) | 100.3 mg/ml (100.3%) |
| Degradants: | | |
| CBE I | NMT 0.2% | ND |
| CBE II | NMT 0.2% | ND |
| OH-CBD | NMT 0.2% | ND |
| Total Degradants | NMT 1.0% | ND |
| Microbial: | | |
| TAMC | NMT $10^3$ cfu/g | Complies with pharmacopoeial requirements |
| TYMC | NMT $10^2$ cfu/g | |
| E. coli | Absent in 1 g | |

ND = Not Detected

TABLE 15

Stability data for CBD 100 mg/ml Oral Solution Batch ET04/126-B In-Use 30° C. ± 2° C./65% RH ± 5% RH, Vertical

| Test | Specification | Time-point (Initial) 8 weeks |
|---|---|---|
| Appearance of Solution | A clear, colorless to yellow solution | A clear solution free from visible particulates |
| CBD Content | 90.0-110.0 mg/ml (90.0-110.0% LC) | 99.7 mg/ml (99.7%) |
| Degradants: | | |
| CBE I | NMT 0.2% | ND |
| CBE II | NMT 0.2% | ND |
| OH-CBD | NMT 0.2% | ND |
| Total Degradants | NMT 1.0% | ND |
| Microbial: | | |
| TAMC | NMT $10^3$ cfu/g | Complies with pharmacopoeial requirements |
| TYMC | NMT $10^2$ cfu/g | |
| E. coli | Absent in 1 g | |

ND = Not Detected

TABLE 16

Stability data for CBD 200 mg/ml Oral Solution Batch ET04/126-C 25° C. ± 2° C./60% RH ± 5% RH, Vertical

| | | Time-point (months) | | | |
|---|---|---|---|---|---|
| Test | Specification | 0 | 2 | 3 | 6 |
| Appearance of Solution | A clear, colorless to yellow solution | A clear solution free from visible particulates | A clear solution free from visible particulates | A clear solution free from visible particulates | A clear solution free from visible particulates |
| CBD Content | 180.0-220.0 mg/ml (90.0-110.0% LC) | 199.5 mg/ml (99.7%) | 202.3 mg/ml (101.2%) | 198.2 mg/ml (99.1%) | 198.3 mg/ml (99.1%) |
| Degradants: | | | | | |
| CBE I | NMT 0.2% | ND | ND | ND | ND |
| CBE II | NMT 0.2% | ND | ND | ND | ND |
| OH-CBD | NMT 0.2% | 0.04% | ND | 0.02% | 0.04% |
| Total Degradants | NMT 1.0% | 0.04% | ND | 0.02% | 0.04% |
| Microbial: | | | | | |
| TAMC | NMT $10^3$ cfu/g | Complies with pharmacopoeial requirements | Complies with pharmacopoeial requirements | Complies with pharmacopoeial requirements | Complies with pharmacopoeial requirements |
| TYMC | NMT $10^2$ cfu/g | | | | |
| E. coli | Absent in 1 g | | | | |

ND = Not Detected

TABLE 17

Stability data for CBD 200 mg/ml Oral Solution Batch ET04/126-C 30° C. ± 2° C./65% RH ± 5% RH, Vertical

| | | Time-point (months) | | | |
|---|---|---|---|---|---|
| Test | Specification | 0 | 2 | 3 | 6 |
| Appearance of Solution | A clear, colorless to yellow solution | A clear solution free from visible particulates | A clear solution free from visible particulates | A clear solution free from visible particulates | A clear solution free from visible particulates |
| CBD Content | 180.0-220.0 mg/ml (90.0-110.0% LC) | 199.5 mg/ml (99.7%) | 201.8 mg/ml (100.9%) | 199.4 mg/ml (99.7%) | 198.0 mg/ml (99.0%) |
| Degradants: | | | | | |
| CBE I | NMT 0.2% | ND | ND | ND | ND |
| CBE II | NMT 0.2% | ND | ND | ND | ND |
| OH-CBD | NMT 0.2% | 0.04% | ND | 0.01% | 0.04% |
| Total Degradants | NMT 1.0% | 0.04% | ND | 0.01% | 0.04% |

TABLE 17-continued

Stability data for CBD 200 mg/ml Oral Solution Batch ET04/126-C 30° C. ± 2° C./65% RH ± 5% RH, Vertical

| | | Time-point (months) | | | |
|---|---|---|---|---|---|
| Test | Specification | 0 | 2 | 3 | 6 |
| Microbial: | | | | | |
| TAMC | NMT $10^3$ cfu/g | Complies with pharmacopoeial requirements | Complies with pharmacopoeial requirements | Complies with pharmacopoeial requirements | Complies with pharmacopoeial requirements |
| TYMC | NMT $10^2$ cfu/g | | | | |
| E. coli | Absent in 1 g | | | | |

ND = Not Detected

TABLE 18

Stability data for CBD 200 mg/ml Oral Solution Batch ET04/126-C 40° C. ± 2° C./75% RH ± 5% RH, Vertical

| | | Time-point (months) | | |
|---|---|---|---|---|
| Test | Specification | 0 | 2 | 6 |
| Appearance of Solution | A clear, colorless to yellow solution | A clear solution free from visible particulates | A clear solution free from visible particulates | A clear solution free from visible particulates |
| CBD Content | 180.0-220.0 mg/ml (90.0-110.0% LC) | 199.5 mg/ml (99.7%) | 202.3 mg/ml (101.2%) | 197.9 mg/ml (99.0%) |
| Degradants: | | | | |
| CBE I | NMT 0.2% | ND | ND | 0.04% |
| CBE II | NMT 0.2% | ND | ND | ND |
| OH-CBD | NMT 0.2% | 0.04% | ND | 0.05% |
| Total Degradants | NMT 1.0% | 0.04% | ND | 0.09% |
| Microbial: | | | | |
| TAMC | NMT $10^3$ cfu/g | Complies with pharmacopoeial requirements | Complies with pharmacopoeial requirements | Complies with pharmacopoeial requirements |
| TYMC | NMT $10^2$ cfu/g | | | |
| E. coli | Absent in 1 g | | | |

ND = Not Detected

TABLE 19

Stability data for CBD 200 mg/ml Oral Solution Batch ET04/126-C In-Use 25° C. ± 2° C./60% RH ± 5% RH, Vertical

| Test | Specification | Time-point (Initial) 8 weeks |
|---|---|---|
| Appearance of Solution | A clear, colorless to yellow solution | A clear solution free from visible particulates |
| CBD Content | 180.0-220.0 mg/ml (90.0-110.0% LC) | 198.7 mg/ml (99.4%) |
| Degradants: | | |
| CBE I | NMT 0.2% | ND |
| CBE II | NMT 0.2% | ND |
| OH-CBD | NMT 0.2% | ND |
| Total Degradants | NMT 1.0% | ND |
| Microbial: | | |
| TAMC | NMT $10^3$ cfu/g | Complies with pharmacopoeial requirements |
| TYMC | NMT $10^2$ cfu/g | |
| E. coli | Absent in 1 g | |

ND = Not Detected

TABLE 20

Stability data for CBD 200 mg/ml Oral Solution (Re-formulation) Batch ET04/126-C In-Use 30° C. ± 2° C./65% RH ± 5% RH, Vertical

| Test | Specification | Time-point (initial) 8 weeks |
|---|---|---|
| Appearance of Solution | A clear, colorless to yellow solution | A clear solution free from visible particulates |
| CBD Content | 180.0-220.0 mg/ml (90.0-110.0% LC) | 199.2 mg/ml (99.6%) |
| Degradants: | | |
| CBE I | NMT 0.2% | ND |
| CBE II | NMT 0.2% | ND |
| OH-CBD | NMT 0.2% | ND |
| Total Degradants | NMT 1.0% | ND |
| Microbial: | | |
| TAMC | NMT $10^3$ cfu/g | Complies with pharmacopoeial requirements |
| TYMC | NMT $10^2$ cfu/g | |
| E. coli | Absent in 1 g | |

ND = Not Detected

Conclusions

From these data it can be concluded that both the 100 mg/ml and the 200 mg/ml CBD containing formulations are stable up to 6 months under both normal and accelerated conditions and the inference is that the formulations will support shelf life of at least:

Climatic Zone I and II—24 months, Store below 25° C.
Climatic Zone III and IV—18 month, Store below 30° C.

Example 6—Safety Levels

The Neotame containing, formulations of Table 8 illustrate the fact that both levels of Neotame and ethanol are well below recommended guidelines when the CBD is used at a dose of 20 mg/kg.

Neotame.

Assuming a maximum CBD dose of 20 mg/kg/day, the maximum Neotame dose at 0.008% w/v concentration in the formulation would be 0.016 mg/kg/day with the 100 mg/ml CBD formulation and 0.008 mg/kg/day with the 200 mg/ml CBD formulation. These are well below the acceptable daily intake limits for Neotame of 0.3 mg/kg/day, as per the FDA guidelines for food.

Ethanol

According to European Medicine Agency draft guideline (EMA/CHMP/507988/2013), for 2-6 years old children a theoretical limit for Blood Alcohol Concentration (BAC) following a single administration of formulation containing alcohol is not more than 0.01 g/L (10 mg/L), and ethanol intake should be exceed 6 mg/kg/day.

The theoretical BAC and maximum ethanol intake for proposed formulations containing 1% v/v ethanol, assuming a max CBD dose of 20 mg/kg/day are detailed in Table 21 below.

TABLE 21

| Formulation | Theoretical BAC | Ethanol intake |
| --- | --- | --- |
| CBD 100 mg/ml solution | 0.001 g/L | 1.58 mg/kg/day |
| CBD 200 mg/ml solution | 0.0005 g/L | 0.79 mg/kg/day |

It is evident that they are well below the specified limits.

The invention claimed is:

1. A method of treating a disease or disorder, the method comprising orally administering to a subject in need thereof a therapeutically effective amount of a pharmaceutical formulation comprising:
cannabidiol (CBD);
a lipid solvent;
an ultrahigh potency sweetener; and
ethanol, wherein ethanol has a concentration of less than about 3% v/v, and
wherein the disease or disorder is epilepsy or a syndrome associated therewith, schizophrenia, tuberous sclerosis complex, brain tumors, neuropathic pain, cannabis use disorder. post-traumatic stress disorder, anxiety, early psychosis, Alzheimer's Disease, or autism.

2. The method of claim 1, wherein the ultrahigh potency sweetener has a sweetness intensity that is 1000× greater than a sweetness intensity of sucrose.

3. The method of claim 1, wherein the ultrahigh potency sweetener has a sweetness intensity that is 5000× greater than a sweetness intensity of sucrose.

4. The method of claim 1, wherein the ultrahigh potency sweetener is (N—[N-(3,3-dimethylbutyl)-L-α-aspartyl]-L-phenylalanine 1-methyl ester) (neotame).

5. The method of claim 1, wherein the ultrahigh potency sweetener is N—[N-3-(3-hydroxy-4methoxyphenyl)propyl-α-L-aspartyl]-L-phenylalanine 1-methyl ester) (advantame).

6. The method of claim 1, further comprising a flavorant.

7. The method of claim 6, wherein the CBD is present in an amount of from 5 to 40% (w/v), the ethanol is present in an amount of less than 2% (v/v), the ultrahigh potency sweetener is present in an amount of less than 0.05% (w/v), the flavorant is present in an amount of less 0.2% (w/v) and the lipid solvent is q.s. to 100%.

8. The method of claim 7, wherein the ultrahigh potency sweetener is Neotame, the flavorant is strawberry flavor and the lipid solvent is sesame oil.

9. The method of claim 1, wherein the formulation is stable in climatic zones I and II for up to 24 months at 25° C.

10. The method of claim 1, wherein the formulation is stable in climatic zones III and IV for up to 18 months at 30° C.

11. The method of claim 1, wherein the solution lacks a stabilizing agent.

12. The method of claim 8, wherein the formulation is stable in climatic zones I and II for up to 24 months at 25° C.

13. The method of claim 8, wherein the formulation is stable in climatic zones III and IV for up to 18 months at 30° C.

14. The method of claim 8, wherein the solution lacks a stabilizing agent.

15. The method of claim 1, the ultrahigh potency sweetener is Neotame, and the lipid solvent is sesame oil.

16. The method of claim 1, wherein the concentration of ethanol is less than about 2% (v/v).

17. The method of claim 1, wherein the concentration of ethanol ranges from about 0.5% (v/v) to 3% (v/v).

18. The method of claim 1, wherein the lipid solvent is sesame oil.

19. The method of claim 1, wherein:
the CBD is present in an amount ranging from 5 to 40% (w/v);
the ethanol is present in an amount ranging from 0.5% (v/v) to 2% (v/v);
the ultrahigh potency sweetener is present in an amount ranging from 0.01% (w/v) to 0.0025%;
flavorant is present in an amount of less 0.2% (w/v); and
sesame oil is q.s. to 100%.

20. The method of claim 1, wherein the CBD is present in an extract.

21. The method of claim 1, wherein the subject is a human.

22. The method of claim 1, wherein the disease or disorder is epilepsy or a syndrome associated therewith.

23. The method of claim 22, wherein the syndrome associated with epilepsy is Dravet Syndrome, Lennox Gastaut Syndrome, myoclonic seizures, juvenile myoclonic epilepsy, refractory epilepsy, juvenile spasms, West syndrome, infantile spasms, or refractory infantile spasms.

24. The method of claim 23, wherein the syndrome is associated with epilepsy is Dravet Syndrome.

25. The method of claim 23, wherein the syndrome is associated with epilepsy is Lennox Gastaut Syndrome.

26. The method of claim 23, wherein the syndrome is associated with epilepsy is tuberous sclerosis complex.

27. The method of claim 23, wherein the syndrome is associated with epilepsy is myoclonic seizures.

* * * * *